United States Patent
Karasawa

(10) Patent No.: US 9,456,841 B2
(45) Date of Patent: Oct. 4, 2016

(54) LIQUID EJECTION CONTROL DEVICE, LIQUID EJECTION SYSTEM, AND CONTROL METHOD

(71) Applicant: SEIKO EPSON CORPORATION, Tokyo (JP)

(72) Inventor: Junichi Karasawa, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/998,145

(22) Filed: Dec. 23, 2015

(65) Prior Publication Data

US 2016/0185109 A1    Jun. 30, 2016

(30) Foreign Application Priority Data

Dec. 24, 2014    (JP) ................ 2014-261256

(51) Int. Cl.
  *A61B 17/22*    (2006.01)
  *A61B 17/3203*    (2006.01)
  *B41J 2/045*    (2006.01)

(52) U.S. Cl.
  CPC ..... *A61B 17/3203* (2013.01); *A61B 17/32037* (2013.01); *B41J 2/04581* (2013.01); *B41J 2/04588* (2013.01)

(58) Field of Classification Search
  CPC ............ A61B 17/32037; A61B 17/22; A61B 7/3203
  See application file for complete search history.

(56) References Cited

U.S. PATENT DOCUMENTS

| 2009/0043480 | A1* | 2/2009 | Seto | A61B 17/3203 701/103 |
| 2010/0069937 | A1 | 3/2010 | Seto et al. | |
| 2014/0107683 | A1* | 4/2014 | Kuhner | B05B 3/14 606/169 |
| 2015/0335344 | A1* | 11/2015 | Aljuri | A61B 17/3203 606/169 |

FOREIGN PATENT DOCUMENTS

| EP | 2 022 419 A2 | 2/2009 |
| EP | 2 783 645 A1 | 10/2014 |
| JP | 2005-152127 A | 6/2005 |

OTHER PUBLICATIONS

Extended European Search Report dated Apr. 21, 2016 as received in Application No. 15201987.3.

* cited by examiner

*Primary Examiner* — Julian Huffman
(74) *Attorney, Agent, or Firm* — Maschoff Brennan

(57) ABSTRACT

In a liquid ejection control device, an operation unit includes a momentum dial for inputting a momentum instructing value related to momentum of a pulsed liquid jet ejected from a liquid ejection device, and a repetitive frequency dial for inputting a repetitive frequency instructing value related to the number of times ejection of the pulsed liquid occurs per unit time. In addition, a controller includes a voltage magnitude setting section that sets voltage magnitude of the drive voltage waveform such that the momentum becomes the momentum instructing value, based on a rising index value related to rising of the drive voltage waveform and the repetitive frequency instructing value.

13 Claims, 17 Drawing Sheets

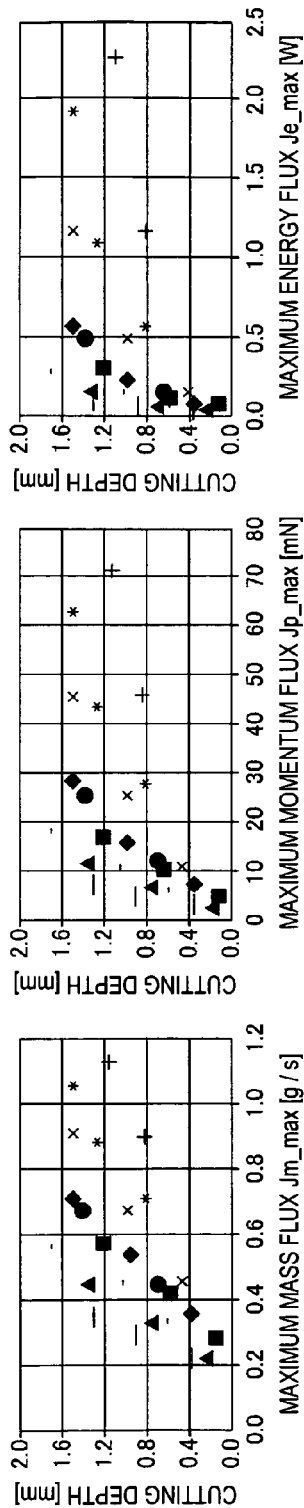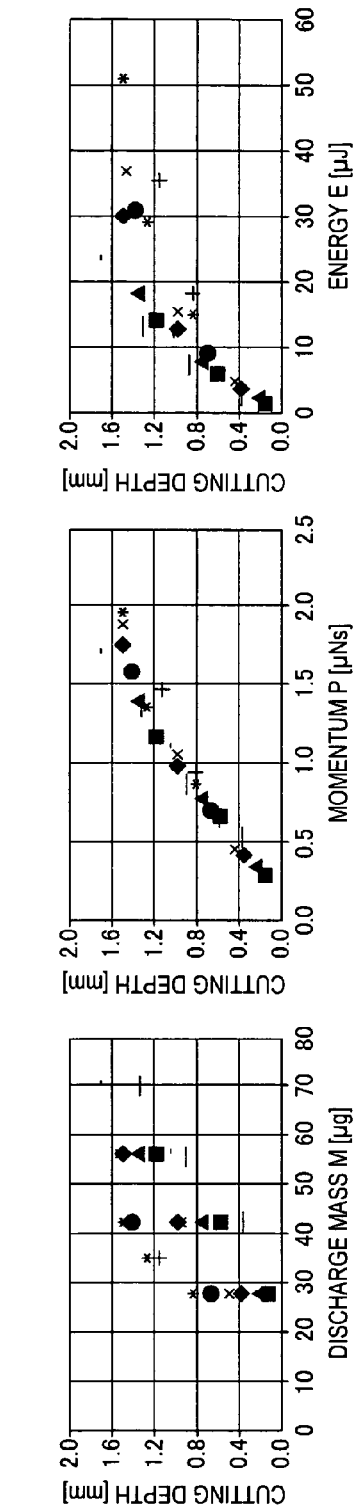
FIG. 6A  FIG. 6C  FIG. 6E
FIG. 6B  FIG. 6D  FIG. 6F

FIG.14

| REPETITIVE FREQUENCY DIAL POSITION | REPETITIVE FREQUENCY INSTRUCTING VALUE | MOMENTUM DIAL POSITION | MOMENTUM INSTRUCTING VALUE | VOLTAGE MAGNITUDE | RISING FREQUENCY |
|---|---|---|---|---|---|
| 1 | F_001 | 1 | P_001 | V_011 | |
| | | 2 | P_002 | V_012 | |
| | | 3 | P_003 | V_013 | |
| | | 4 | P_004 | V_014 | |
| | | 5 | P_005 | V_015 | |
| 2 | F_002 | 1 | P_001 | V_021 | |
| | | 2 | P_002 | V_022 | |
| | | 3 | P_003 | V_023 | |
| | | 4 | P_004 | V_024 | |
| | | 5 | P_005 | V_025 | |
| 3 | F_003 | 1 | P_001 | V_031 | |
| | | 2 | P_002 | V_032 | |
| | | 3 | P_003 | V_033 | f_001 |
| | | 4 | P_004 | V_034 | |
| | | 5 | P_005 | V_035 | |
| 4 | F_004 | 1 | P_001 | V_041 | |
| | | 2 | P_002 | V_042 | |
| | | 3 | P_003 | V_043 | |
| | | 4 | P_004 | V_044 | |
| | | 5 | P_005 | V_045 | |
| 5 | F_005 | 1 | P_001 | V_051 | |
| | | 2 | P_002 | V_052 | |
| | | 3 | P_003 | V_053 | |
| | | 4 | P_004 | V_054 | |
| | | 5 | P_005 | V_055 | |

| REPETITIVE FREQUENCY DIAL POSITION | REPETITIVE FREQUENCY INSTRUCTING VALUE | MOMENTUM DIAL POSITION | MOMENTUM INSTRUCTING VALUE | RISING FREQUENCY DIAL POSITION | RISING FREQUENCY INSTRUCTING VALUE | VOLTAGE MAGNITUDE |
|---|---|---|---|---|---|---|
| 1 | F_011 | 1 | P_011 | 1 | f_011 | V_111 |
|   |   |   |   | 2 | f_012 | V_112 |
|   |   |   |   | 3 | f_013 | V_113 |
|   |   |   |   | 4 | f_014 | V_114 |
|   |   |   |   | 5 | f_015 | V_115 |
|   |   | 2 | P_012 | 1 | f_011 | V_121 |
|   |   |   |   | 2 | f_012 | V_122 |
|   |   |   |   | 3 | f_013 | V_123 |
|   |   |   |   | 4 | f_014 | V_124 |
|   |   |   |   | 5 | f_015 | V_125 |
|   |   | ... | ... | ... | ... | ... |
|   |   | 5 | P_015 | 1 | f_011 | V_151 |
|   |   |   |   | 2 | f_012 | V_152 |
|   |   |   |   | 3 | f_013 | V_153 |
|   |   |   |   | 4 | f_014 | V_154 |
|   |   |   |   | 5 | f_015 | V_155 |
| 1 | F_012 | 1 | P_011 | 1 | f_011 | V_211 |
|   |   |   |   | 2 | f_012 | V_212 |
|   |   |   |   | 3 | f_013 | V_213 |
|   |   |   |   | 4 | f_014 | V_214 |
|   |   |   |   | 5 | f_015 | V_215 |
|   |   | ... | ... | ... | ... | ... |
|   |   | 5 | P_015 | 1 | f_011 | V_251 |
|   |   |   |   | 2 | f_012 | V_252 |
|   |   |   |   | 3 | f_013 | V_253 |
|   |   |   |   | 4 | f_014 | V_254 |
|   |   |   |   | 5 | f_015 | V_255 |
| ... | ... | ... | ... | ... | ... | ... |

LIQUID EJECTION CONTROL DEVICE, LIQUID EJECTION SYSTEM, AND CONTROL METHOD

PRIORITY INFORMATION

The present invention claims priority to Japanese Patent Application No. 2014-261256 filed Dec. 24, 2014, which is incorporated herein by reference in its entirety.

BACKGROUND

1. Technical Field

The present invention relates to a liquid ejection control device that controls a liquid ejection device which uses a piezoelectric element and ejects a liquid having a pulsed shape.

2. Related Art

A technology, in which a liquid is ejected using a pulsed shape ejection pulse in order to cut a cutting target object, is known. Ejection of a liquid to have a pulsed shape means a jet flow of liquid is ejected from a nozzle in a pulsating manner, and thus, in this specification, the ejection is properly referred to as a "pulsed liquid jet."

The pulsed liquid jet is variously used, and, for example, JP-A-2005-152127 proposes a technology which is used for performing surgery in the medical field. In this case, the cutting target object is a living tissue and the liquid is saline.

A mechanism which uses a piezoelectric element is one of the known mechanisms which is used to generate a pulsed liquid jet. In the mechanism, drive voltage having a pulsed wave shape is applied to a piezoelectric element and thereby, the piezoelectric element generates momentary pressure such that the liquid is ejected in a pulsed shape. Accordingly, in a case where strength of a pulsed liquid jet is changed, the drive voltage which is applied to the piezoelectric element is controlled. Therefore, it is conceivable to use a type of mechanism in which a characteristic value of the drive voltage which is applied to the piezoelectric element, such as a magnitude of a drive voltage waveform (voltage magnitude, also referred to as a size of drive voltage) is controlled by an operation unit such as an operation dial, an operation button, or the like, and thereby the strength of the pulsed liquid jet is changeable.

However, even when the characteristic value of the drive voltage which is controlled by the operation unit is changed, it is often not possible to change a cutting mode such as a cutting depth or a cutting volume of the cutting target object as intended by a user. A detailed description thereof will be provided below, and, for example, in many instances even when a user changes the voltage magnitude to be twice or four times, or half or one fourth of the magnitude, the cutting depth or the cutting volume is not necessarily changed at equivalent amounts. In a case where the pulsed liquid jet is used for surgery, a problem arises in that a surgeon's operation sense does not work as intended.

Meanwhile, if an ejection cycle of the pulsed liquid jet is changeable, it is possible to increase or decrease a cutting depth or a cutting volume per unit time and it is possible to adjust a speed of cutting a cutting target object. However, since the shape of the drive voltage waveform is changed when the ejection cycle is changed, the strength of a liquid jet for one pulse or the like can change. Accordingly, the cutting depth or the cutting volume obtained by a pulsed liquid jet for one pulse changes before and after the ejection cycle is changed, which can result in a case where a cutting speed proportional to an ejection frequency intended by a user is not obtained even when the ejection cycle is short, that is, when the ejection frequency is high.

SUMMARY

An advantage of some aspects of the invention is to propose a technology in which strength of a pulsed liquid jet can be set as intended by a user and usability is improved.

A first aspect of the invention is directed to a liquid ejection control device in which a predetermined drive voltage waveform is applied to a piezoelectric element to control the ejection of a pulsed liquid jet of liquid having a pulsed shape from a liquid ejection device that uses the piezoelectric element. The liquid ejection control device includes a first operation unit for inputting a first instructing value related to momentum of the pulsed liquid jet, a second operation unit for inputting a second instructing value related to the number of times of an ejection of the pulsed liquid is performed per unit time, and a voltage magnitude setting section that sets voltage magnitude of the drive voltage waveform such that the momentum becomes the first instructing value, based on an index value related to rising of the drive voltage waveform and the second instructing value.

As another aspect of the invention, the invention may be configured as a control method in which a predetermined drive voltage waveform is applied to a piezoelectric element to control the ejection of a pulsed liquid jet of liquid having a pulsed shape from a liquid ejection device that uses the piezoelectric element. The control method includes inputting a first instructing value related to momentum of the pulsed liquid jet, inputting a second instructing value related to the number of times ejection of the pulsed liquid is performed per unit time, and setting voltage magnitude of the drive voltage waveform such that the momentum becomes the first instructing value, based on an index value related to rising of the drive voltage waveform and the second instructing value.

According to the first aspect of the invention, when the first instructing value related to the momentum of the pulsed liquid jet and the second instructing value related to the number of times of ejection of the pulsed liquid is performed per unit time are input, the voltage magnitude of the drive voltage waveform is set such that the momentum becomes the first instructing value based on the index value related to the rising of the drive voltage waveform and the second instructing value. As will be described below, a cutting depth or a cutting volume is closely related to the momentum of the pulsed liquid jet. Accordingly, direct instruction of the momentum of the pulsed liquid jet enables a cutting depth or a cutting volume, which meets a user's intention or operational sense, to be realized and enables usability to be improved.

In addition, it is possible to select the number of times of ejection of the pulsed liquid per unit time is performed. In this manner, for example, it is possible to increase or decrease the number of times ejection is performed per unit of time while the first instructing value is maintained. Accordingly, it is possible to adjust a cutting speed without change in the cutting depth or the cutting volume by the pulsed liquid jet for one pulse before and after the number of times of ejection is changed and improvement of usability is achieved.

A second aspect of the invention is directed to the first aspect of the invention, in which the liquid ejection control device further includes a third operation unit for inputting a third instructing value related to the index value.

According to the second aspect of the invention, it is possible to input the third instructing value related to the index value of the drive voltage waveform.

A third aspect of the invention is directed to the first or second aspect of the invention, in which the liquid ejection control device further includes a falling shape setting section that changeably sets a falling shape of the drive voltage waveform depending on the second instructing value.

According to the third aspect of the invention, the falling shape of the drive voltage waveform is changeably set, and thereby it is possible to control the repeating ejection of the pulsed liquid jets such that the number of times of ejection of the pulsed liquid is performed per unit time becomes the second instructing value while a predetermined or desirable rising shape of the drive voltage waveform is maintained.

A fourth aspect of the invention is directed to any one of the first to third aspects of the invention, in which the liquid ejection control device further includes a display control unit that performs control of display of at least one of the first instructing value and the second instructing value.

According to the fourth aspect of the invention, it is possible to display at least one of the first instructing value related to the momentum of the pulsed liquid jet and the second instructing value related to the number of times of ejection of the pulsed liquid is performed per unit time. In this manner, it is possible to visually check momentum of the current pulsed liquid jet instructed by a user or the index indicating the number of times of ejection per unit time. Accordingly, it is possible to further improve usability.

A fifth aspect of the invention is directed to any one of the first to fourth aspects of the invention, in which the liquid ejection device is controlled such that momentum of the pulsed liquid jet is from 2 nNs (nanonewton seconds) to 2 mNs (millinewton seconds) or kinetic energy is from 2 nJ (nanojules) to 200 mJ (millijules).

According to the fifth aspect of the invention, the momentum of the pulsed liquid jet is from 2 nNs to 2 mNs or the kinetic energy is from 2 nJ to 200 mJ and it is possible to control the liquid ejection device in the above range. In this manner, it is suitable for cutting a flexible material such as a living tissue or food, a gel material, or a resin material such as rubber, or plastics.

A sixth aspect of the invention is directed to any one of the first to fifth aspects of the invention, in which the liquid ejection device is controlled to cut a living tissue by the pulsed liquid jet.

According to the sixth aspect of the invention, for example, it is possible to control the strength of the pulsed liquid jet suitable for surgery.

A seventh aspect of the invention is directed to a liquid ejection system including the liquid ejection control device according to any one of the first to sixth aspects of the invention, a liquid ejection device, and a feeding pump device.

According to the seventh aspect of the invention, it is possible to realize the liquid ejection system in which the effects of the operations according to the first to sixth aspects are achieved.

BRIEF DESCRIPTION OF THE DRAWINGS

The invention will be described with reference to the accompanying drawings, wherein like numbers reference like elements.

FIGS. 6A to 6F are diagrams showing simulation results (cutting depths);

FIG. 14 is a diagram showing an example of a data configuration of a momentum conversion table according to Example 1;

FIG. 18 is a diagram showing an example of a data configuration of a momentum conversion table according to Example 2.

DESCRIPTION OF EXEMPLARY EMBODIMENTS

Hereinafter, a configuration for realizing a liquid ejection control device, a liquid ejection system, and a control method according to the invention will be described. Further, the invention is not limited to the embodiments to be described below and a configuration which is applicable to the invention is not limited to the following embodiments, either. In addition, in description of the drawings, the same signs are assigned to the same components.

Overall Configuration

Figure 1:
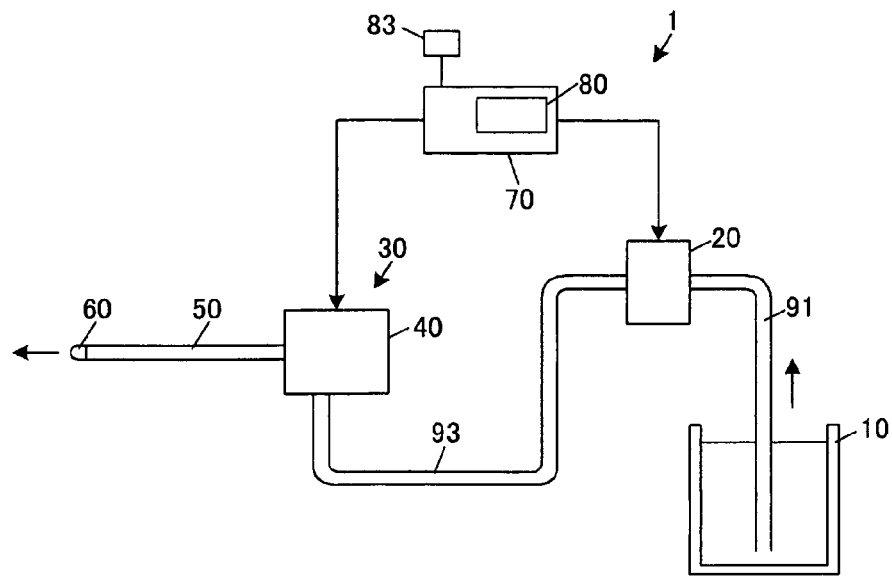
FIG. 1 is a view showing an example of an entire configuration of a liquid ejection system.

FIG. 1 is a view showing an example of an entire configuration of a liquid ejection system 1 according to one embodiment of the invention. The liquid ejection system is used for cutting work of a flexible material, for example, for surgery in which a living tissue is a cutting target object, for a food process in which food is the cutting target object, for processing of a gel material or for cutting work of a resin material such as rubber or plastics. In the liquid ejection system, a pulsed liquid jet having momentum in a range from 2 [nNs (nanonewton seconds)] to 2 [mNs (millinewton seconds)] or kinetic energy in a range from 2 [nJ (nanojules)] to 200 [mJ (millijules)] is ejected and the cutting target object is cut. Hereinafter, a case where a liquid ejection system 1 is used for surgery to perform incision, excision, or lithotripsy (collectively referred to as "cutting") of an affected area (living tissue) is illustrated. In addition, in description according to the embodiment, momentum flux and momentum indicate scalar quantity in which only an ejecting direction component of a pulsed liquid jet is considered, that is, a size.

As shown in FIG. 1, the liquid ejection system 1 includes a container 10 which contains a liquid, a feeding pump device 20, a liquid ejection device 30 for ejecting the liquid having a pulsed shape toward a cutting target object, and a liquid ejection control device 70.

In the liquid ejection system 1, the liquid ejection control device 70 includes an operation panel 80 on which a surgeon operates during surgery. The operation panel 80 is used for inputting various operations such as an increase/decrease operation of the momentum. In addition, the liquid ejection control device 70 includes an ejection pedal 83 which is used for switching between ejection start and ejection stop of the pulsed liquid jet by being pressed with a surgeon's foot.

The container 10 contains a liquid such as water, saline, or liquid medicine. The feeding pump device 20 supplies the liquid contained in the container 10 invariably at a predetermined pressure and at a predetermined flow rate through connection tubes 91 and 93 to a pulse flow generator 40 of the liquid ejection device 30.

The liquid ejection device 30 is a section (hand piece) which is gripped and operated by a surgeon during surgery and includes a pulse flow generator 40 which applies pulsation to the liquid supplied from the feeding pump device 20 and generates a pulse flow, and a pipe-like ejection tube 50. The liquid ejection device 30 ejects the pulse flow generated by the pulse flow generator 40 as a pulsed liquid jet through the ejection tube 50 and, finally, through a liquid ejection opening 61 (refer to FIG. 2) provided in a nozzle 60.

Here, the pulse flow means a pulsating flow of a liquid in which the flow velocity or pressure of the liquid significantly and rapidly changes in terms of time. Similarly, ejection of a liquid having a pulsed shape means pulsating ejection of the liquid in which the flow velocity of the liquid passing through a nozzle significantly changes in terms of time. In the embodiment, a case where a pulsed liquid jet generated by applying cyclic pulsation to a steady flow is described; however, the invention can be similarly applied to sporadic or intermittent ejection of the pulsed liquid jets in which ejection and non-ejection of the liquid are repeated.

Figure 2:
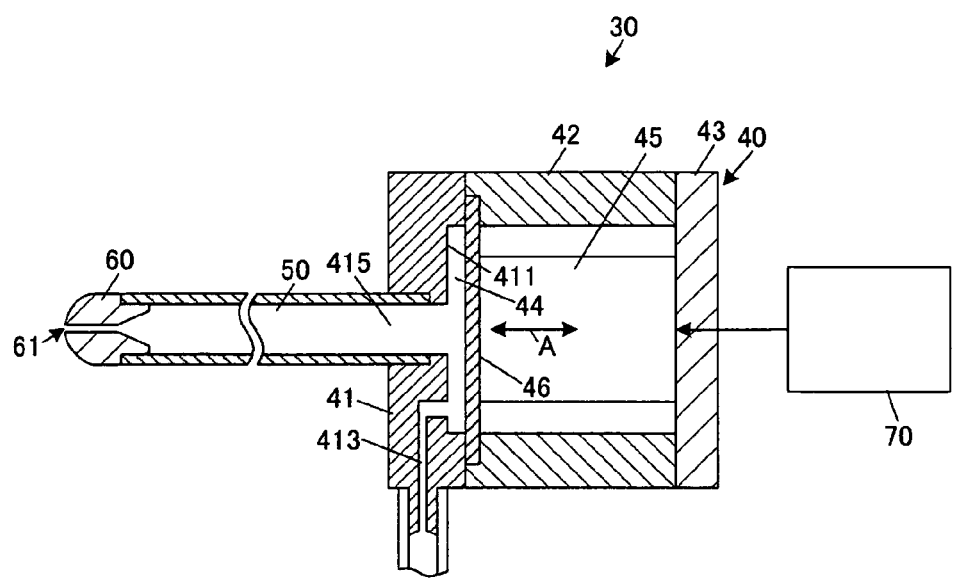
FIG. 2 is a view showing an internal structure of a liquid ejection device.

FIG. 2 is a cross-sectional view illustrating a cross-section of the liquid ejection device 30 in order to illustrate the internal configuration of the liquid ejection device 30, the cross-section being sectioned in an ejection direction. Further, components or portions shown in FIG. 2 have a vertical and horizontal scale different from that in reality, for convenience of drawing. As shown in FIG. 2, the pulse flow generator 40 has a configuration in which a piezoelectric element 45 and a diaphragm 46 for changing the volume of a pressure chamber 44 are disposed in a cylindrical inside space formed by a first case 41, a second case 42, a third case 43. The cases 41, 42, and 43 are joined on surfaces facing each other and are integrated.

The diaphragm 46 is a disc-shaped thin metal plate and an outer circumferential portion thereof is interposed and fixed between the first case 41 and the second case 42. The piezoelectric element 45 is, for example, a stacked piezoelectric element and one end thereof is fixed to the diaphragm 46 between the diaphragm 46 and the third case 43 and the other end thereof is fixed to the third case.

The pressure chamber 44 is a space surrounded by the diaphragm 46 and a recessed section 411 formed in a surface facing the diaphragm 46 of the first case 41. An inlet channel 413 and an outlet channel 415 which communicate with the pressure chamber 44 are formed in the first case 41. An inner diameter of the outlet channel 415 is formed to be greater than an inner diameter of the inlet channel 413. The inlet channel 413 is connected to the connection tube 93 and guides the liquid supplied from the feeding pump device 20 to the pressure chamber 44. One end of the ejection tube 50 is connected to the outlet channel 415 and the liquid which flows in the pressure chamber 44 is guided to the ejection tube 50. The nozzle 60, which includes the liquid ejection opening 61 having an inner diameter smaller than an inner diameter of the ejection tube 50, is inserted into the other end (distal end) of the ejection tube 50.

In the liquid ejection system 1 configured as above, under control by the liquid ejection control device 70, the liquid contained in the container 10 is supplied at a predetermined pressure or at a predetermined flow rate by the feeding pump device 20 to the pulse flow generator 40 through the connection tube 93. Meanwhile, when a drive signal is applied to the piezoelectric element 45 under the control by the liquid ejection control device 70, the piezoelectric element 45 expands and contracts (arrow A in FIG. 2). Since the drive signal applied to the piezoelectric element 45 is repetitively applied at a predetermined repetitive frequency (for example, tens of [Hz] to hundreds of [Hz]), the expansion and contraction of the piezoelectric element 45 are repeated for each cycle. In this manner, pulsation is applied to the steady flow of the liquid flowing in the pressure chamber 44 and the pulsed liquid jets are repetitively ejected from the liquid ejection opening 61.

Figure 3A:
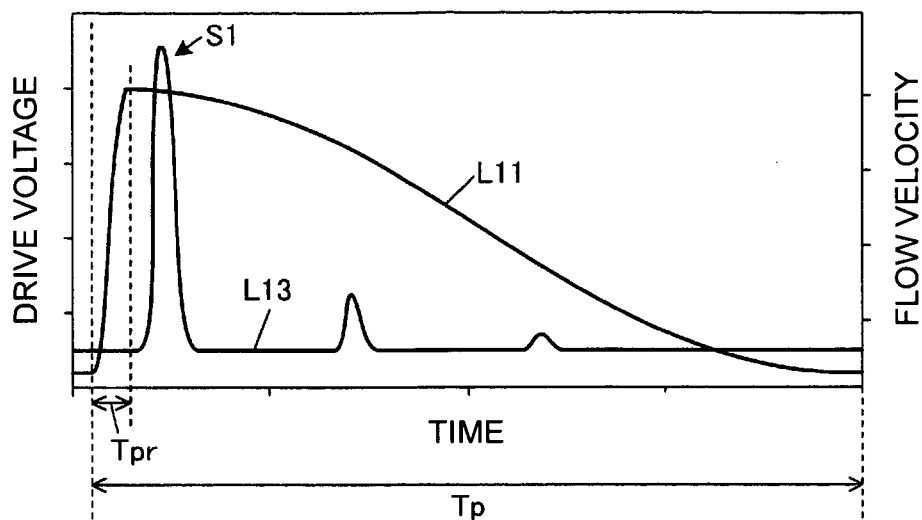
FIGS. 3A and 3B are diagrams showing a drive voltage waveform for one cycle of a piezoelectric element and a flow velocity waveform of a liquid at a liquid ejection opening.
Figure 3B:
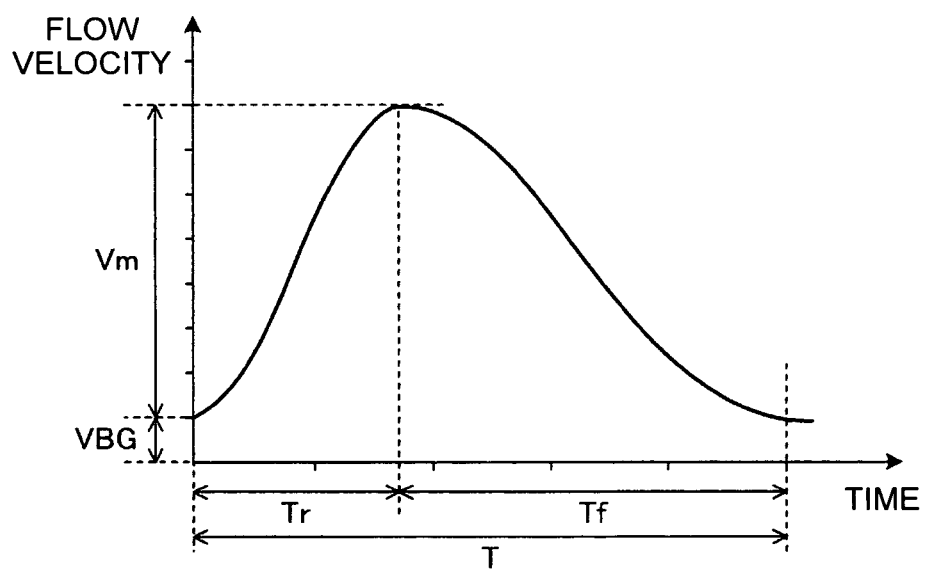

FIG. 3A is a diagram showing an example of a drive voltage waveform L11 of a drive signal for one cycle, which is applied to the piezoelectric element 45 and also showing a flow velocity waveform L13 of the liquid in the liquid ejection opening 61. In addition, FIG. 3B is a diagram showing a flow velocity waveform (central peak portion) S1 having the highest peak, which is taken from the peak of the flow velocity waveform L13 in FIG. 3A.

Tp shown in FIG. 3A represents a repetitive cycle (time for one cycle of the drive voltage waveform) and a reciprocal of Tp means the repetitive frequency described above. Further, a repetitive cycle Tp becomes about 1 [ms (millisecond)] to 100 [ms] and time (rising time) Tpr required for the drive voltage waveform to rise to the maximum voltage becomes about 10 [μs (microseconds)] to 1000 [μs (microseconds)]. The repetitive cycle Tp is set to be a period of time longer than the rising time Tpr. In addition, when a reciprocal of the rising time Tpr is the rising frequency, the repetitive frequency is set as a frequency lower than the rising frequency. The rising frequency and the rising time are index values (rising index values) related to rising of the drive voltage.

For example, when the piezoelectric element 45 expands in a case where a positive voltage is applied, the piezoelectric element rapidly extends during rising time Tpr and the diaphragm 46 is pushed by the piezoelectric element 45 and is bent toward the pressure chamber 44 side. When the diaphragm 46 is bent to the pressure chamber 44 side, the volume of the pressure chamber 44 becomes smaller and the liquid in the pressure chamber 44 is pushed out from the pressure chamber 44. Here, since the inner diameter of the outlet channel 415 is greater than the inner diameter of the inlet channel 413, the fluid inertance and fluid resistance of the outlet channel 415 is smaller than the fluid resistance of the inlet channel 413. Accordingly, most of the liquid pushed out from the pressure chamber 44 through rapid expansion of the piezoelectric element 45 is guided to the ejection tube 50 through the outlet channel 415, and then a liquid droplet having a pulsed shape, that is, a pulsed liquid jet, is formed by the liquid ejection opening 61 having a diameter smaller than the inner diameter of the ejection tube and is ejected at a high speed.

After the voltage is increased to the maximum voltage, the drive voltage is gradually lowered. Then, the piezoelectric element 45 is contracted over a period of time longer than the rising time Tpr and the diaphragm 46 is pulled by the piezoelectric element 45 and is bent to the third case 43 side. When the diaphragm 46 is bent to the third case 43 side, the volume of the pressure chamber 44 is increased and the liquid is guided into the pressure chamber 44 from the inlet channel 413.

Further, since the feeding pump device 20 supplies the liquid at the predetermined pressure or at the predetermined flow rate to the pulse flow generator 40, the liquid (steady flow) flowing in the pressure chamber 44 is guided to the ejection tube 50 through the outlet channel 415 and is ejected from the liquid ejection opening 61 when the piezoelectric element 45 does not perform expansion and contraction operations. Since the ejection is performed as a liquid flow at a constant and low speed, the liquid flow is referred to as the steady flow.

Principle

A value, by which the pulsed liquid jet is characterized, is based on both the drive voltage waveform L11 and the flow velocity waveform L13 of a jet for one pulse in the liquid ejection opening 61 shown in FIG. 3A. The central peak portion (a jet of the peak wave) having the maximum flow velocity, which is generated immediately after rising of the drive voltage taken from FIG. 3B, is noticeable. Another low peak is formed due to a jet which is ejected collaterally through back and forth reflection of a wave having pressure fluctuation, which is generated in the pressure chamber 44 at the time of expansion of the piezoelectric element 45, within the ejection tube 50; however, what determines a cutting mode such as a cutting depth or a drive voltage of the cutting target object is the jet (hereinafter, referred to as a primary jet) of the peak wave in which the flow velocity is greatest.

However, in a case where strength of the pulsed liquid jet is changed such that the cutting depth or the cutting volume of the cutting target object is changed, the drive voltage waveform of the piezoelectric element 45 is controlled. It is conceivable to employ a method in which the control of the drive voltage waveform is performed by a surgeon who instructs a rising frequency of the drive voltage waveform or magnitude (voltage magnitude) of the drive voltage waveform as a voltage characteristic value thereof. For example, it is conceivable to employ a method in which a surgeon instructs the rising frequency (or, the rising time Tpr) at a state at which the voltage magnitude is fixed, or the surgeon instructs the voltage magnitude in a state in which the rising frequency is fixed. This is because the voltage magnitude or the rising frequency (rising time Tpr) thereof has a significant influence on a flow velocity waveform of the primary jet. After the drive voltage is increased to the maximum voltage, the drive voltage gradually lowered from the maximum voltage has little influence on the flow velocity waveform of the primary jet. Accordingly, when the rising frequency becomes high or the voltage magnitude is increased, it is considered that the cutting depth is increased and the cutting volume is increased proportional thereto.

However, a cutting depth or a cutting volume of the cutting target object is not necessarily changed in proportion to the increase and decrease of the voltage characteristic value in some cases, and as such, usability deteriorates. For example, a case can be brought about, in which the cutting depth or the cutting volume is not increased as expected even when a surgeon increases the voltage magnitude two times or the cutting depth or the cutting volume is not decreased as designed even when the voltage magnitude is decreased to be half. Accordingly, there can be an occurrence of a situation in which a surgeon does not achieve a desirable cutting depth or cutting volume. This is a problem which results in extension of surgery time.

In addition, there is a case in which a cutting speed needs to be adjusted, independent of the strength of the pulsed liquid jet. As a type of method for this, it is conceivable to employ a method in which a surgeon instructs the repetitive frequency of the drive voltage waveform. For example, to increase the repetitive frequency means that the number of times of ejection of the pulsed liquid jets per unit time is increased, and the finally achieved cutting depth or cutting volume is changed.

However, the drive voltage waveform is changed when the repetitive frequency is changed. Therefore, even when the repetitive frequency is changed, the cutting depth or the cutting volume per unit time is not changed in proportion thereto and a surgeon performs surgery with deteriorated usability. Specifically, it is conceivable to employ a method in which the entire drive voltage waveform is simply extended and contracted in a time axis direction, and thereby the repetitive frequency is changed. However, in this method, since the rising frequency which has a significant influence on the flow velocity waveform of the primary jet is likely to be changed, the strength of the pulsed liquid jet is likely to be changed as described above. Accordingly, a cutting speed is not achieved in proportion to the repetitive frequency, as intended.

Therefore, the flow velocity waveform of the primary jet is focused and correlations between several parameters, which are determined depending on the flow velocity waveform of the primary jet, and the cutting depth and the cutting volume are examined. This is because it is possible to control the piezoelectric element 45 with the optimum drive voltage waveform for achieving the cutting depth or the cutting volume as exact as a surgeon's operation sense when a parameter having a close correlation with the cutting depth or the cutting volume is found.

First, mass flux [kg/s], momentum flux [N], and energy flux [W] of the primary jet passing through the liquid ejection opening 61 are examined, based on a flow velocity waveform v [m/s] of the primary jet in the liquid ejection opening 61. The mass flux corresponds to a mass [kg/s] of the liquid passing through the liquid ejection opening 61 per unit time. The momentum flux corresponds to momentum [N] of the liquid passing through the liquid ejection opening 61 per unit time. The energy flux corresponds to energy [W] of the liquid passing through the liquid ejection opening 61 per unit time. Further, the energy indicates the kinetic energy, and, hereinafter, is abbreviated to "energy".

Since the liquid is released to a free space from the liquid ejection opening 61, pressure can be set nearly to "0". In addition, a speed in a direction (radial direction of the liquid ejection opening 61) orthogonal to a jet ejecting direction of the liquid can be set nearly to "0". When it is assumed that the liquid has no speed distribution in the radial direction of the liquid ejection opening 61, it is possible to obtain mass flux Jm [kg/s], momentum flux Jp [N], and energy flux Je [W] of passing through the liquid ejection opening 61 by the following equations (1), (2), and (3). S [m$^2$] represents a sectional area of a nozzle and ρ [kg/m$^3$] represents working fluid density.

$$Jm = S \cdot \rho \cdot v \quad (1)$$

$$Jp = S \cdot \rho \cdot v^2 \quad (2)$$

$$Je = \frac{1}{2} \cdot \rho \cdot S \cdot v^3 \quad (3)$$

Figure 4A:
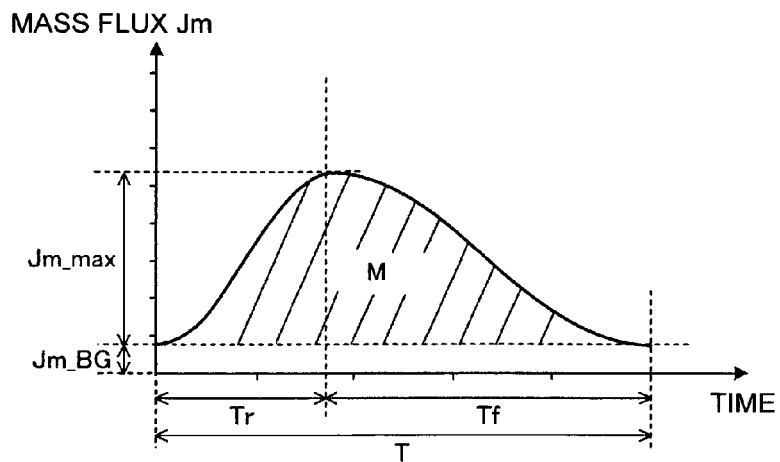
FIGS. 4A to 4C are diagrams showing mass flux, momentum flux, and energy flux.
Figure 4B:
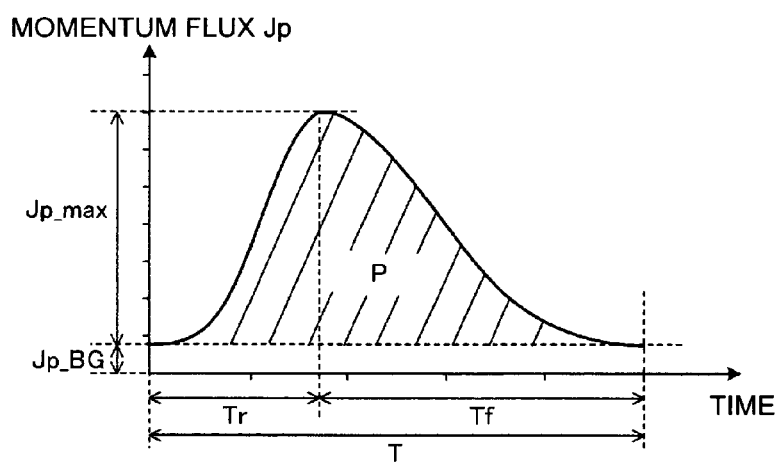
Figure 4C:
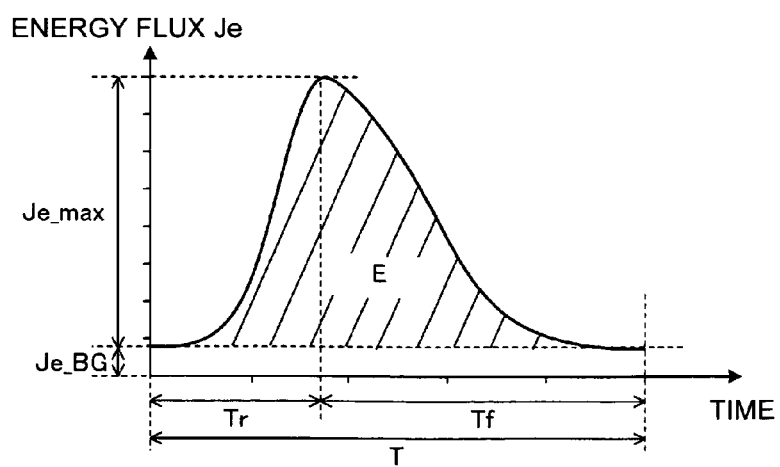

FIGS. 4A to 4C are diagrams showing mass flux Jm (4A), momentum flux Jp (4B), and energy flux Je (4C) which are obtained from the flow velocity waveform of the primary jet shown in FIG. 3B. When the mass flux Jm, the momentum flux Jp, and the energy flux Je are integrated, respectively, within a period of time (duration time) T from rising to falling of the flow velocity waveform of the primary jet, it is possible to obtain mass, momentum, and energy of the liquid ejected from the liquid ejection opening 61, as the primary jet.

It is conceivable that the cutting depth and the cutting volume by a jet for one pulse can be determined from the respective values of the mass flux Jm, the momentum flux Jp, the energy flux Je, the mass, the momentum, and the energy which are calculated in the manner described above. Here, all the values are a physical quantity containing amount corresponding to the steady flow and, more importantly, are values obtained by excluding an amount corresponding to contribution to the steady flow.

Therefore, in terms of mass flux Jm in FIG. 4A, two parameters of the maximum mass flux Jm_max [kg/s] obtained by subtracting mass flux Jm_BG [kg/s] of the steady flow from the peak value (maximum value) of the mass flux Jm, and discharge mass M [kg], which is obtained by subtracting the amount corresponding to the steady flow from mass of the liquid discharged as the primary jet from the liquid ejection opening 61 and is shown by being hatched in FIG. 4A, are defined. The discharge mass M is represented by the following equation (4).

$$M = \int (Jm - Jm\_BG) dt \quad (4)$$

In terms of momentum flux Jp in FIG. 4B, two parameters of the maximum momentum flux Jp_max [N] obtained by subtracting momentum flux Jp_BG [N] of the steady flow from the peak value (maximum value) of the momentum flux Jp, and momentum P [Ns], which is obtained by excluding the amount corresponding to the steady flow from momentum of the liquid discharged as the primary jet from the liquid ejection opening 61 and is shown by being hatched in FIG. 4B, are defined. The momentum P is represented by the following equation (5).

$$P = \int (Jp - Jp\_BG) dt \quad (5)$$

In terms of energy flux Je in FIG. 4C, two parameters of the maximum energy flux Je_max [W] obtained by subtracting energy flux Je_BG [W] of the steady flow from the peak value (maximum value) of the energy flux Je, and energy E [J], which is obtained by subtracting the amount corresponding to the steady flow from energy of the liquid discharged as the primary jet from the liquid ejection opening 61 and is shown by being hatched in FIG. 4C, are defined. The energy E is represented by the following equation (6).

$$E = \int (Je - Je\_BG) dt \quad (6)$$

Here, an integration section in the above equations (4), (5), and (6) is time (duration time) T from rising to falling of the primary jet in the respective flow velocity waveforms.

Therefore, it is examined how closely the six parameters of the maximum mass flux Jm_max, the discharge mass M, the maximum momentum flux Jp_max, the momentum P, the maximum energy flux Je_max, and the energy E are correlated with the cutting depth and the cutting volume, respectively, using a numerical simulation.

Here, the pulsed liquid jet is a fluid and the cutting target object is a flexibly elastic body. Accordingly, an appropriate breakdown threshold value is set on the flexibly elastic body side so as to perform a simulation of breakdown behavior of the cutting target object by the pulsed liquid jet, and so-called interaction analysis (fluid/structure interaction analysis (FSI)) of a fluid and a structure (here, a flexibly elastic body) has to be performed. Examples of a calculation technique of the simulation include a technique using a finite element method (FEM), a technique using a particle method represented by smoothed particle hydrodynamics (SPH) or the like, a technique of combination of the finite element method and the particle method, or the like. There is no particular limitation on a technique applied here, and thus detailed description thereof is not provided; however, the optimal technique was selected taking into account stability of an analysis result, calculation time, or the like, and the simulation was performed.

On the occasion of the simulation, fluid density was set to 1 [g/cm$^3$], a diameter of the liquid ejection opening 61 was set to 0.15 [mm], and a standoff distance (distance from the liquid ejection opening 61 to the surface of the cutting target object) was set to 0.5 [m]. In addition, it was assumed that the surface of the cutting target object was a flexibly elastic flat body, and, as a physical model thereof, a Mooney-Rivlin hyperelastic body having modulus of elasticity of about 9 [kPa] (about 3 [kPa] in shear modulus conversion) in Young's modulus conversion, when density was set to 1 [g/cm$^3$], was used. As the breakdown threshold value, deviation equivalent strain was set to 0.7.

According to the flow velocity waveform of the primary jet, various flow velocity waveforms of the primary jets are assumed and a total of 27 types were prepared in terms of three types of waveforms of a sine wave, a triangle wave, and a rectangular wave which are modified to have three types of magnitudes (the maximum value of the flow velocity) in a range of 12 [m/s] to 76 [m/s] and to have three types of duration time in a range of 63 [μs] to 200 [μs]. Further, the flow velocity of the steady flow is set to 1 [m/s].

Figure 5A:
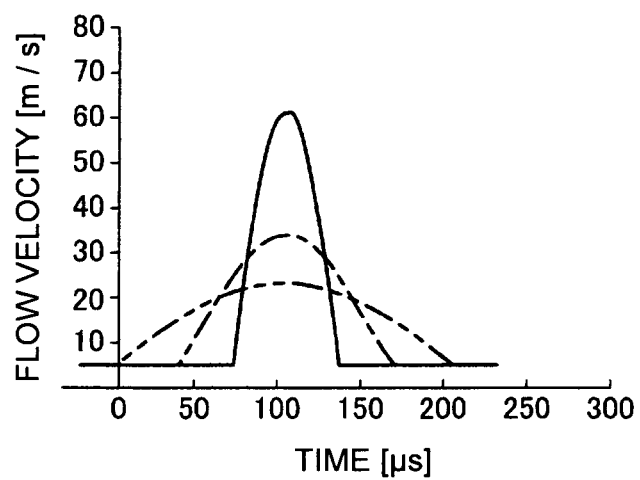
FIGS. 5A to 5C are diagrams showing a flow velocity waveform of a primary jet which is used in a simulation of a cutting mode of a cutting target object.
Figure 5B:
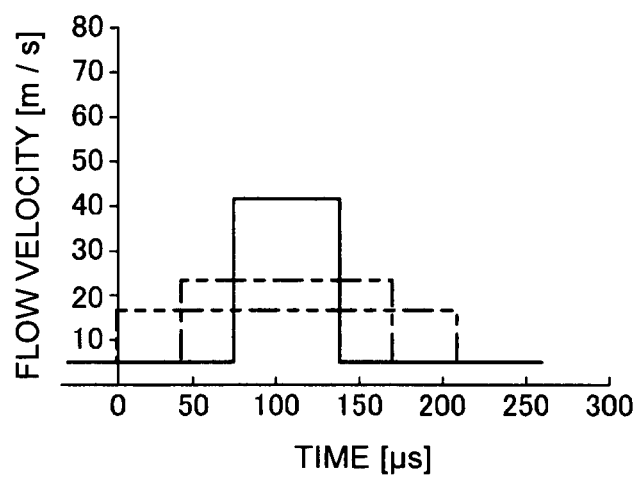
Figure 5C:
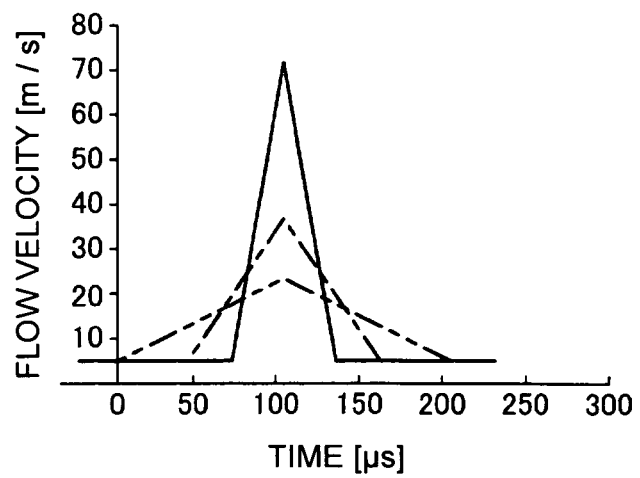

FIGS. 5A to 5C are diagrams showing a sine wave (5A), a rectangular wave (5B), and a triangular wave (5C) which are applied as the flow velocity waveform of the primary jet in the simulation. A wave of which the duration time shown in a solid line is 63 [μs], a wave of which the duration time shown in a dashed line is 125 [μs], and a wave of which the duration time shown in a two-dot chain line is 200 [μs] were prepared. Therefore, a pulsed liquid jet to which the prepared waveform is applied as the flow velocity waveform of the primary jet was generated, a simulation of breakdown behavior of the flexibly elastic body, when the jet is ejected to the flexibly elastic body, was performed, and examination of the cutting depth or the cutting volume was performed.

FIGS. 6A to 6F are diagrams showing simulation results which are plotted, in which the vertical axis represents the cutting depth of the cutting target object and the horizontal axis represents the maximum mass flux Jm_max (6A), the discharge mass M (6B), the maximum momentum flux Jp_max (6C), the momentum P (6D), the maximum energy flux Je_max (6E), and the energy E (6F). In FIGS. 6A to 6F, a simulation result obtained when a sine wave having the duration time of 63 [μs] is applied as the flow velocity waveform of the primary jet is plotted as a "*", a simulation result obtained when a sine wave having 125 [μs] is applied is plotted as a "♦", a simulation result obtained when a sine wave having 200 [μs] is applied is plotted as a "–". In addition, a simulation result obtained when a triangle wave having the duration time of 63 [μs] is applied as the flow velocity waveform of the primary jet is plotted as a "+", a simulation result obtained when a triangle wave having 125 [μs] is applied is plotted as a "×", a simulation result obtained when a triangle wave having 200 [μs] is applied is plotted as a "■". In addition, a simulation result obtained when a rectangular wave having the duration time of 63 [μs] is applied as the flow velocity waveform of the primary jet is plotted as a "●", a simulation result obtained when a rectangular wave having 125 [μs] is applied is plotted as a black triangle, a simulation result obtained when a rectangular wave having 200 [μs] is applied is plotted as a "–".

As shown in FIGS. 6A, 6C, and 6E on the upper stage, it turns out that relationships between three respective parameters of the maximum mass flux Jm_max, the maximum momentum flux Jp_max, and the maximum energy flux Je_max and the cutting depth are not close because dispersion thereof becomes great due to the shape of the waveform applied as the flow velocity waveform of the primary jet. Particularly, since the mass flux is a value proportional to the flow velocity, it is indicated that the cutting depth is not determined only by the maximum flow velocity of the primary jet.

Next, when relationships between three respective parameters of the discharge mass M, the momentum P, and the energy E shown in FIGS. 6B, 6D, and 6F on the lower stage and the cutting depth are considered, the relationship between the discharge mass M and the cutting depth is not close because dispersion thereof becomes great by the shape of the waveform applied as the flow velocity waveform of the primary jet. In comparison, in terms of the relationship with the momentum P and the energy E, dispersion is small by the shape of the applied waveform and the respective plots are distributed substantially on the same curve. In terms of the momentum P and the energy E, the momentum P has less dispersion. Accordingly, the cutting depth has a close correlation with the momentum P or the energy E and, particularly, has a strong correlation with the momentum P.

Further, the simulation was performed in a case where the diameter of the liquid ejection opening was 0.15 [mm] and the standoff distance was 0.5 [mm]; however, the simulation was performed with a different diameter of the liquid ejection opening or a different standoff distance and it was confirmed that a qualitative inclination, in which the cutting depth has a close correlation with the momentum P or the energy E, was not significantly changed.

FIGS. 7A to 7F are diagrams showing simulation results which are plotted, in which the vertical axis represents the cutting volume of the cutting target object and the horizontal axis represents the maximum mass flux Jm_max (7A), the discharge mass M (7B), the maximum momentum flux Jp_max (7C), the momentum P (7D), the maximum energy flux Je_max (7E), and the energy E (7F). The relationships between the shapes applied as the flow velocity waveform of the primary jet and the types of plots are the same as those in FIGS. 6A to 6F.

Figure 7E:
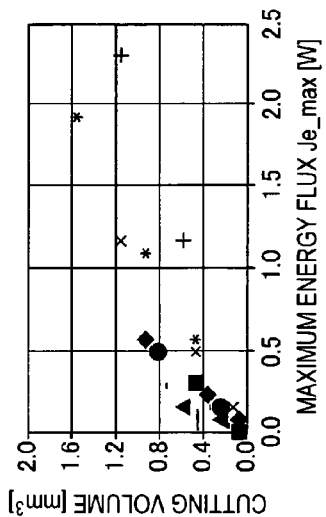
FIGS. 7A to 7F are diagrams showing simulation results (cutting volume)
Figure 7C:
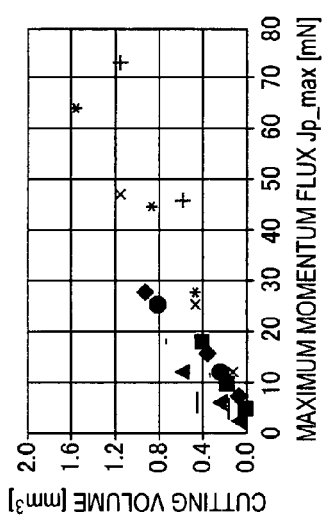
Figure 7A:
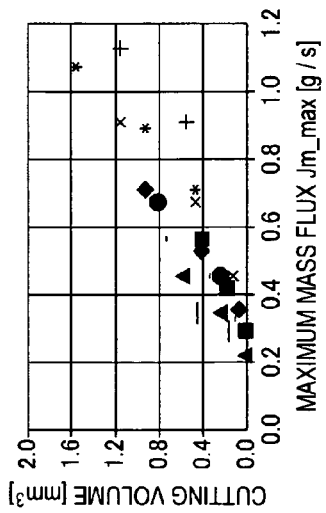

As shown in FIGS. 7A, 7C, and 7E on the upper stage, it is considered that relationships between three respective parameters of the maximum mass flux Jm_max, the maximum momentum flux Jp_max, and the maximum energy flux Je_max and the cutting volume are not close, although the relationships are closer than those with the cutting depth, because dispersion thereof occurs by shapes of waveforms applied as the flow velocity waveform of the primary jet.

Figure 7F:
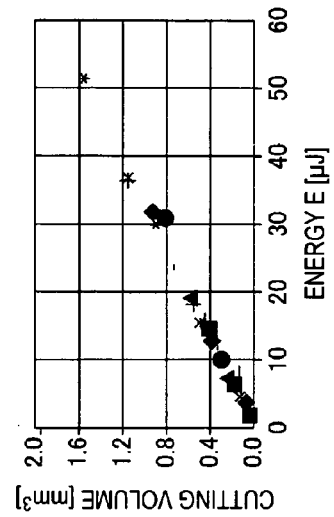
Figure 7D:
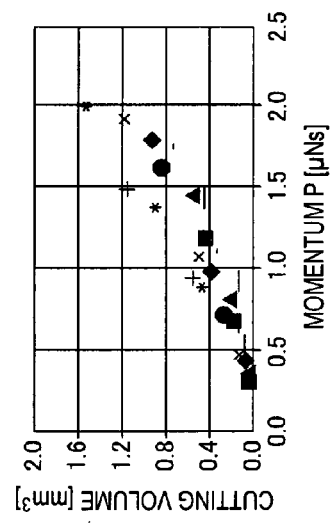
Figure 7B:
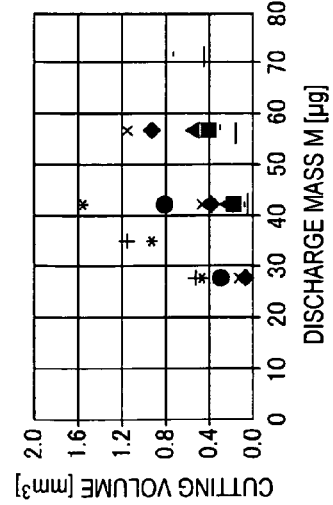

Next, when relationships between three respective parameters of the discharge mass M, the momentum P, and the energy E shown in FIGS. 7B, 7D, and 7F on the lower stage and the cutting volume are considered, the relationship between the discharge mass M and the cutting volume is not close because dispersion thereof becomes great by the shapes of the waveforms applied as the flow velocity waveform of the primary jet, similar to the cutting depth. Meanwhile, in terms of the relationship with the momentum P and the energy E, dispersion is small by the shapes of the applied waveforms, similar to the cutting depth, and the respective plots are distributed substantially on the same straight line. In addition, the energy E has less dispersion, compared to the momentum P. Accordingly, the cutting volume has a close correlation with the momentum P or the energy E and, particularly, has a strong correlation with the momentum P.

Further, the simulation was performed in a case where the diameter of the liquid ejection opening was 0.15 [mm] and the standoff distance was 0.5 [mm]; however, the simulation was performed with a different diameter of the liquid ejection opening or a different standoff distance and it was confirmed that a qualitative inclination, in which the cutting volume has a close correlation with the momentum P or the energy E, was not significantly changed.

Based on the above examination results, in the embodiment, the momentum P is focused. Also, a simulation is performed in advance with a representative waveform as the drive voltage waveform which is actually applied to the piezoelectric element 45 and a correspondence relationship among the momentum P, the rising frequency, the voltage magnitude, and the repetitive frequency is obtained.

For this reason, first, a control parameter was changeably set and a flow velocity waveform of the primary jet was obtained through a simulation. The simulation can be easily performed using a numerical simulation by using an equivalent circuit method based on a model in which a channel system of the liquid ejection device is replaced with fluid (channel) resistance, fluid inertance, fluid compliance, or the like. Otherwise, if higher accuracy is required, a fluid simulation using a finite element method (FEM), a finite volume method (FVM), or the like, may be used.

Figure 8A:
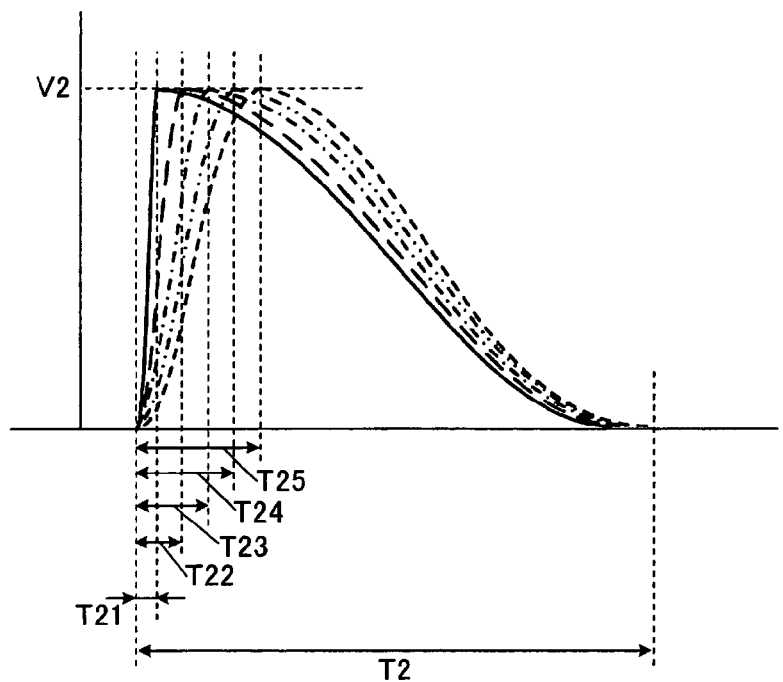
FIGS. 8A and 8B are diagrams showing simulation results of the flow velocity waveform of the primary jet in a case where drive voltage waveforms of different rising frequencies are applied.

First, the voltage magnitude and the repetitive frequency were fixed, a drive voltage waveform generated by changing the rising frequency in a stepwise manner was applied, and a flow velocity waveform of the primary jet was obtained through a simulation. FIG. 8A is a diagram showing an example of the applied drive voltage waveform. The respective drive voltage waveforms are generated when the voltage magnitude is set to V2, a repetitive cycle Tp is set to T2, and the rising time Tpr is extended from T21 to T25 in a stepwise manner (the rising frequency is lowered in a stepwise manner).

Figure 8B:
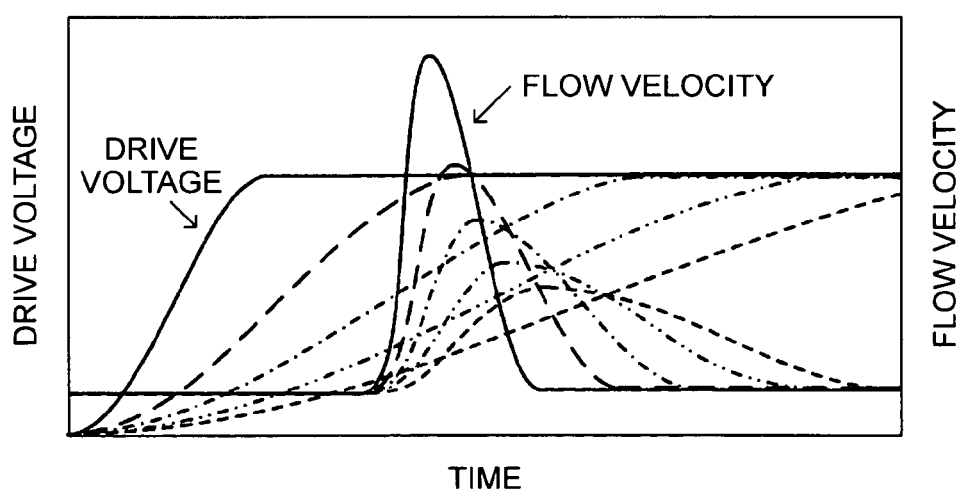

FIG. 8B is a diagram showing a simulation result of the flow velocity waveform of the primary jet in a case where respective drive voltage waveforms having different rising frequencies shown in FIG. 8A are applied. As shown in FIG.

8B, when the rising frequency is lowered (the rising time Tpr is extended), the flow velocity waveform of the primary jet has a start timing of rising which is not changed and has extended duration time to the rising and has the flow velocity magnitude (maximum value of the flow velocity) which becomes smaller.

Figure 9A:
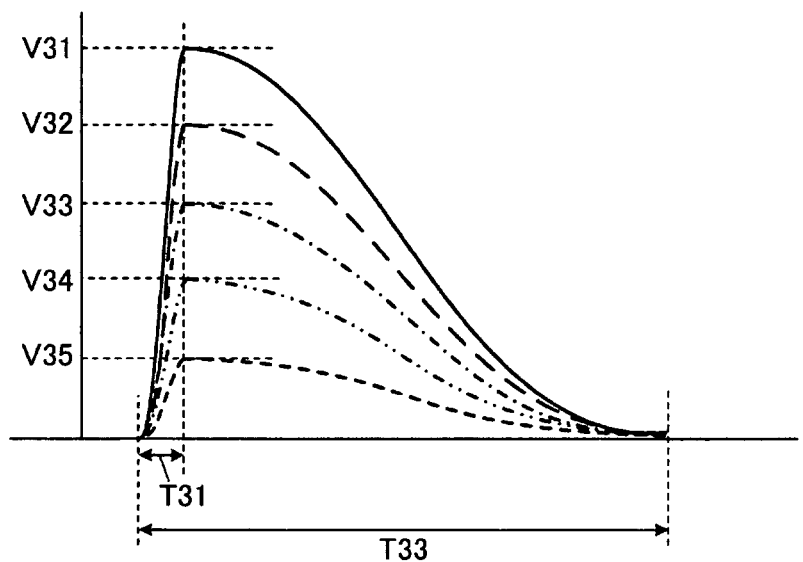
FIGS. 9A and 9B are diagrams showing simulation results of the flow velocity waveform of the primary jet in a case where drive voltage waveforms of different voltage magnitude are applied.

Second, the rising frequency and the repetitive frequency were fixed, a drive voltage waveform generated by changing the voltage magnitude in a stepwise manner was applied, and a flow velocity waveform of the primary jet was obtained through a simulation. FIG. 9A is a diagram showing an example of the applied drive voltage waveform. The respective drive voltage waveforms are generated when the rising time Tpr is set to T31, a repetitive cycle Tp is set to T33, and the voltage magnitude is decreased from V31 to V35 in a stepwise manner.

Figure 9B:
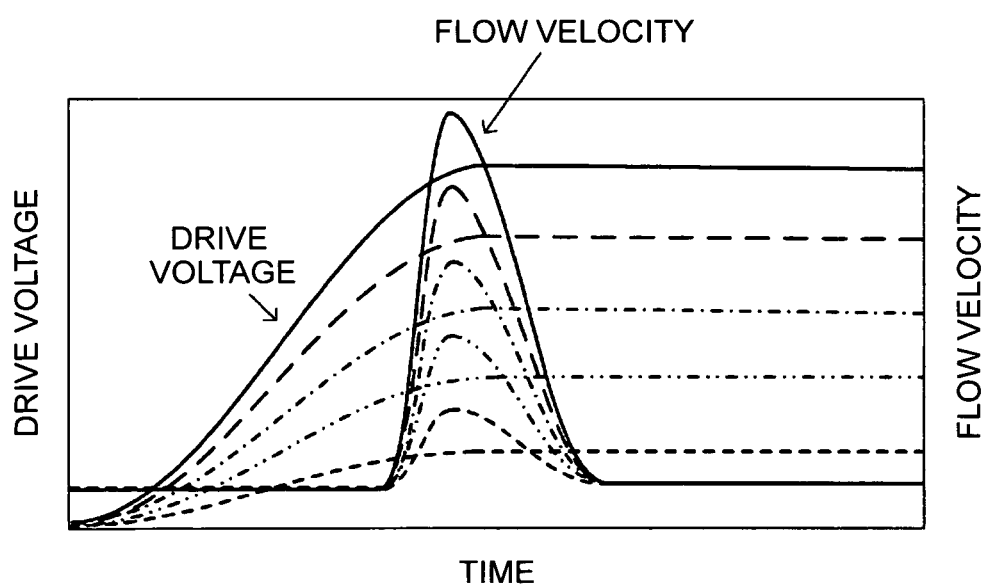

FIG. 9B is a diagram showing a simulation result of the flow velocity waveform of the primary jet in a case where drive voltage waveforms having different voltage magnitudes shown in FIG. 9A are applied. As shown in FIG. 9B, when the voltage magnitude is decreased, in the flow velocity waveform of the primary jet, which is different from that in the case where the rising frequency is lowered, duration time for rising is maintained and the flow velocity magnitude (maximum value of the flow velocity) becomes smaller.

Figure 10A:
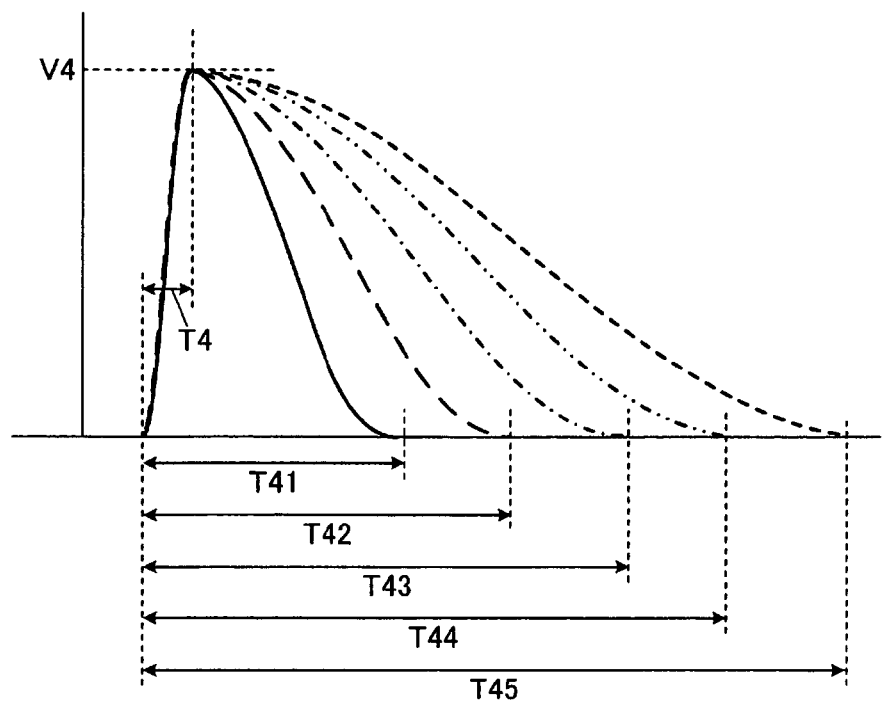
FIGS. 10A and 10B are diagrams showing simulation results of the flow velocity waveform of the primary jet in a case where drive voltage waveforms of different repetitive frequencies are applied.

Third, the rising frequency and the voltage magnitude were fixed, a drive voltage waveform generated by changing the repetitive frequency in a stepwise manner was applied, and a flow velocity waveform of the primary jet was obtained through a simulation. FIG. 10A is a diagram showing an example of the applied drive voltage waveform. The respective drive voltage waveforms are generated when the rising time Tpr is set to T4, the voltage magnitude is set to V4, and the repetitive cycle Tp extended from T41 to T45 in a stepwise manner (the repetitive frequency is lowered) in a stepwise manner by widening a rising shape in the time axis direction after the drive voltage is increased to the maximum voltage.

Figure 10B:
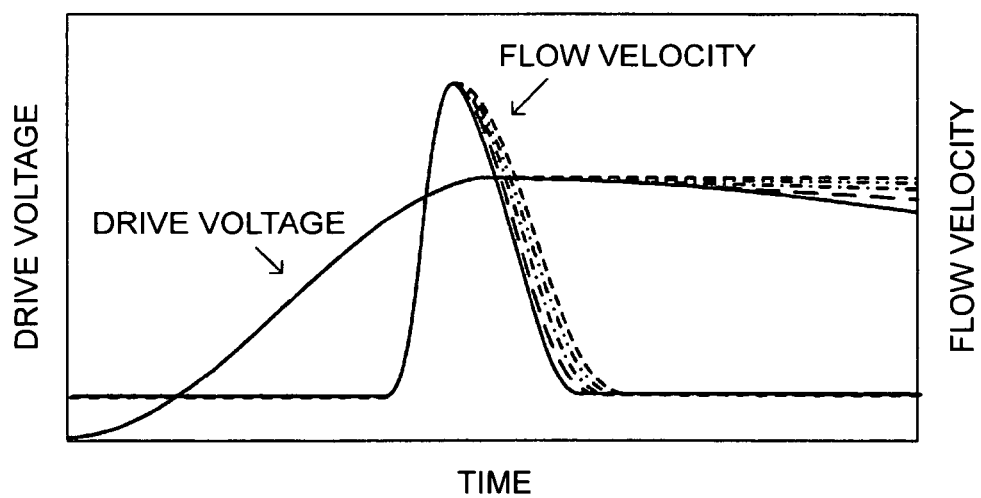

FIG. 10B is a diagram showing a simulation result of the flow velocity waveform of the primary jet in a case where drive voltage waveforms having different repetitive frequencies shown in FIG. 10A are applied. As shown in FIG. 10B, when the repetitive frequency is lowered (the repetitive cycle Tp is extended), the flow velocity waveform of the primary jet has extended duration time which is not as long as that in a case where the rising frequency is lowered. The flow velocity magnitude (maximum value of the flow velocity) is maintained.

Subsequently, momentum P was obtained for each flow velocity waveform of the obtained primary jet. To be more exact, while the repetitive frequency was changed in the manner described with reference to FIGS. 10A and 10B, both simulation cases where the voltage magnitude was fixed and the rising frequency was changed in the manner described with reference to FIGS. 8A and 8B and a simulation where the rising frequency is fixed and the voltage magnitude is changed in the manner described with reference to FIGS. 9A and 9B, were performed for each repetitive frequency. Also, momentum P of the flow velocity waveform of the primary jet obtained through each simulation was obtained.

Figure 11:
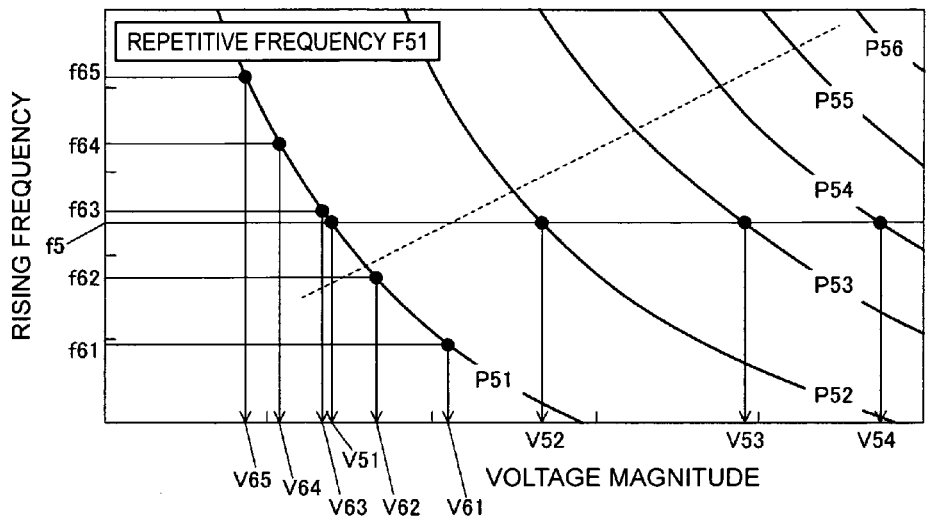
FIG. 11 is a diagram showing a correspondence relationship between momentum P, a rising frequency, and a voltage magnitude, at a predetermined repetitive frequency.

FIG. 11 is a diagram showing a correspondence relationship among momentum P, the rising frequency, and the voltage magnitude, obtained at the predetermined repetitive frequency (for example, described as "F51"). FIG. 11 is made by depicting contour lines related to the momentum P on a coordinate space with the vertical axis representing the rising frequency, and the horizontal axis representing the voltage magnitude. The momentums P51, P52, and the like on each contour line become less towards the lower left and become greater by a predetermined amount towards the upper right in FIG. 11. Further, although not shown, if the momentums P obtained at another repetitive frequency are plotted at the same coordinate space and depicted with contour lines, a contour line diagram is obtained in terms of a correspondence relationship among the momentums P, the rising frequencies, and the voltage magnitudes at the repetitive frequency.

Here, what is focused is that the momentums P are not linearly changed with respect to a parameter in each coordinate axis direction. For example, in the correspondence relationship between the momentums P, the rising frequencies, and the voltage magnitudes shown in FIG. 11, a case is conceivable, in which the rising frequency is fixed (for example, f5), the voltage magnitude is changeable, and the drive voltage waveform of the piezoelectric element 45 is controlled. In a case where an amount of change of the momentums P is constant, a voltage magnitude change between the voltage magnitudes V51 and V52 is required between the momentums P51 and P52 and a voltage magnitude change between the voltage magnitudes V52 and V53 is required between the momentums P52 and P53. However, a voltage magnitude interval of the voltage magnitudes V51 and V52 is different from a voltage magnitude interval of the voltage magnitudes V52 and V53. This phenomenon remarkably occurs as the momentum P is increased. Accordingly, when the rising frequency is fixed and an operation of changing the voltage magnitude by a constant amount is performed, the momentum P is not changed as intended, which results in a situation in which the cutting depth or the cutting volume is not changed as intended by a surgeon or as exact as a surgeon's sense. The same is true for the case where the voltage magnitude is fixed and an operation of changing the rising frequency by a constant amount is performed.

Therefore, in an embodiment of the present invention, as an operation performed by a surgeon during surgery, at least an increase/decrease operation of the momentum P and an increase/decrease operation of the repetitive frequency momentum P are received and a table of the correspondence relationships between the momentum P, the rising frequencies, and the voltage magnitudes for the respective repetitive frequencies on the contour lines obtained for the respective repetitive frequencies described above is made in advance. Also, in response to the increase/decrease operation of the momentum P and the increase/decrease operation of the repetitive frequency by a surgeon, the rising frequency and the voltage magnitude corresponding to the momentum P indicated from the correspondence relationship according to the instructed repetitive frequency are specified and driving of the piezoelectric element 45 is controlled.

Example 1

Figure 12:
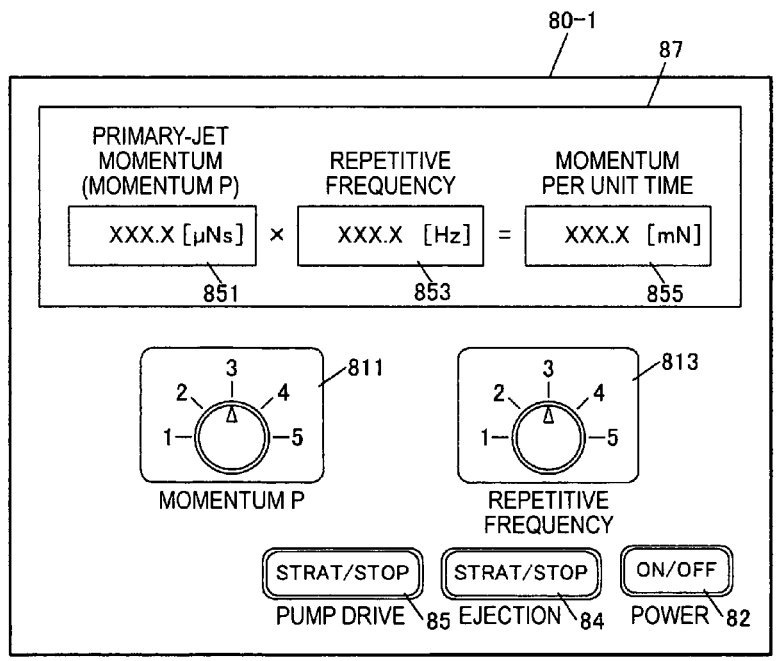
FIG. 12 is a diagram showing an operation panel of a liquid ejection control device according to Example 1.

First, Example 1 is described. FIG. 12 is a diagram showing an operation panel 80-1 which is provided in a liquid ejection control device 70-1 according to Example 1. As shown in FIG. 12, on the operation panel 80-1, a momentum dial 811 as a first operation unit, a repetitive frequency dial 813 as a second operation unit, a power button 82, an ejection button 84, a pump drive button 85, and a liquid crystal monitor 87 are disposed.

The momentum dial 811 is for inputting an instructing value of momentum P (momentum instructing value) as a first instructing value, and has a configuration in which five-level dial positions, to which, for example, scales of "1" to "5" are assigned, are selectable. A surgeon increases or decreases the momentum P in five levels by switching between the dial positions of the momentum dial 811. For example, a momentum instructing value is allocated to each position of the dial in advance such that the momentum is increased by a constant amount in proportion to a numerical value on a corresponding scale. Further, the number of levels of the dial positions is not limited to five and may be appropriately set such as three levels of "large", "intermediate", and "small", or possibly adjustment with no level.

The repetitive frequency dial 813 is for inputting an instructing value of a repetitive frequency (repetitive frequency instructing value) as a second instructing value, and, similar to the momentum dial 811, has a configuration in which five-level dial positions of "1" to "5" are selectable. Further, when it is assumed that a surgeon mainly performs the increase/decrease operation of the momentum P, the repetitive frequency dial 813 may be configured to include an activate switch for switching between validity and invalidity of an operation with respect to the repetitive frequency dial 813. The surgeon increases or decreases, in five levels, the repetitive frequency (for example, from tens of [Hz] to hundreds of [Hz]) of the drive voltage waveform repetitively applied to the piezoelectric element 45 by switching between the dial positions of the repetitive frequency dial 813. For example, a repetitive frequency instructing value is allocated to each position of the dial in advance such that the repetitive frequency is increased by a constant amount in proportion to a numerical value on a corresponding scale. Further, the number of levels of the dial positions is not limited to five and the number of levels may be appropriately set. In addition, the number of levels may be different from that of the momentum dial 811.

In this manner, in Example 1, two operations performed by a surgeon during surgery are the increase/decrease operation of the momentum P using the momentum dial 811 and the increase/decrease operation of the repetitive frequency using the repetitive frequency dial 813. Also, the rising frequency is fixed, and a table of the correspondence relationships between the momentums P and the voltage magnitudes at a predetermined rising frequency for each repetitive frequency is made in advance. For example, in a case where the rising frequency is f5 shown in FIG. 11, the voltage magnitudes V51, V52, and the like at intersection points A51, A52, and the like, with each contour line are associated with the momentums P51, P52, and the like on the corresponding contour lines, the rising frequency is set to f5, and a data table at the repetitive frequency F51 is made. Data tables are made for other repetitive frequencies in the same manner.

Here, the rising frequency is fixed and a data table is made. In comparison, a table may be made by determining a reference line in the coordinate space shown in FIG. 11 and acquiring the rising frequency and the voltage magnitude at each intersection point at which the reference line intersects with each contour line of the momentum P. For example, in a case where a straight line illustrated in a dotted line shown in FIG. 11 is the reference line, the rising frequencies and the voltage magnitudes at intersection points with each contour line are associated with the momentums P51, P52, and the like on the corresponding contour line and a data table thereof may be made. Further, the reference line illustrated in the dotted line in FIG. 11 may not be a straight line, for example, may be a curve.

Also, the respective momentums P51, P52 and the like on the respective contour lines are allocated as the momentum instructing value in ascending order to the dial positions 1, 2, and the like of the momentum dial 811. Accordingly, the momentum P can be changed by an amount of the same extent when the momentum dial 811 moves to a position one scale apart.

Meanwhile, the respective repetitive frequencies listed on the data table are allocated as the repetitive frequency instructing value in the order from the lower value to the dial positions 1, 2, and the like of the repetitive frequency dial 813. For example, when the repetitive frequency dial 813 moves through the scales without a movement of the momentum dial 811, it is possible to adjust a cutting speed without changing the momentum P.

The power button 82 is for switching between ON and OFF of the power. The ejection button 84 is for switching between the ejection start and the ejection stop of the pulsed liquid jet and provides the same function as that of the ejection pedal 83 shown in FIG. 1. The pump drive button 85 is for switching between supply start and supply stop of the liquid to the liquid ejection device 30 from the feeding pump device 20.

In addition, on the liquid crystal monitor 87 of the operation panel 80-1, a display screen, which displays the momentum P, that is, primary jet momentum [μNs] 851 for one pulse, a repetitive frequency [Hz] 853, momentum per unit time, which is obtained by multiplying the momentum and the repetitive frequency, that is, a force [mN] 855, is displayed, and current values of the respective values (hereinafter, collectively referred to as momentum information) are renewed and displayed. Here, a value displayed in the primary jet momentum 851 is the current value of the momentum instructing value and a value displayed on the repetitive frequency 853 is the repetitive frequency instructing value. A surgeon can check the current values of the momentum P, the repetitive frequency, or the momentum (force) per unit time, related to the pulsed liquid jet ejected from the liquid ejection opening 61, on the display screen during surgery and can perform operations.

Further, as shown in FIG. 12, on the display screen during surgery, three values of the momentum P, the repetitive frequency, and the momentum P per unit time need not to be displayed and a configuration in which at least one of the momentum P and the repetitive frequency is displayed may be employed. In addition, one or both of the current rising frequency (or rising time Tpr) and the voltage magnitude, as well as the momentum P or the repetitive frequency, may be together displayed. In addition, the display of the respective values is not limited to a case of performing by the display of the numerical values shown in FIG. 12, the display may be performed by a meter display or changes of the momentum P, the repetitive frequency, or the like along with the increase/decrease operation from the ejection start of the pulsed liquid jet may be displayed as a graph.

Figure 13:
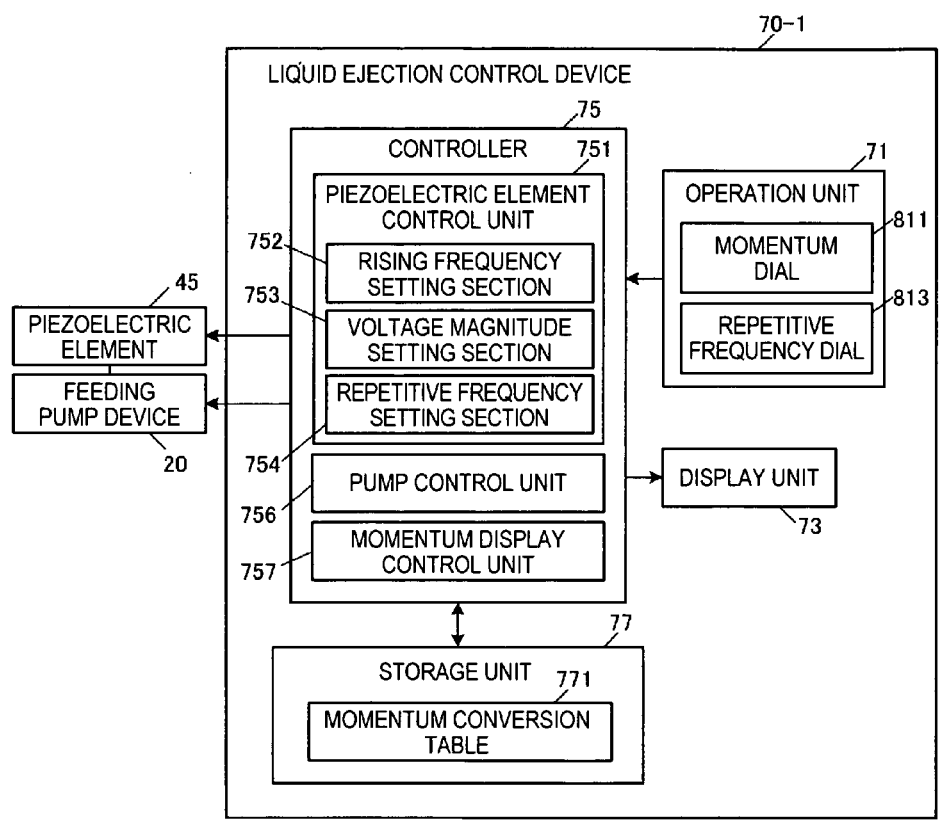
FIG. 13 is a block diagram showing an example of a functional configuration of the liquid ejection control device according to Example 1.

FIG. 13 is a block diagram showing an example of a functional configuration of the liquid ejection control device according to Example 1. As shown in FIG. 13, the liquid ejection control device 70-1 includes an operation unit 71, a display unit 73, a controller 75, and a storage unit 77.

The operation unit 71 is realized by various switches such as a button switch, a lever switch, a dial switch, a pedal switch, input devices such as a touch panel, a trackpad, a mouse, or the like, and an operation signal in response to an operation input is output to the controller 75. The operation unit 71 includes the momentum dial 811 and the repetitive frequency dial 813. In addition, although not shown, the operation unit 71 includes the ejection pedal 83 in FIG. 1, the power button 82, the ejection button 84 and the pump drive button 85 on the operation panel 80-1 shown in FIG. 12.

The display unit 73 is realized by a display device such as a liquid crystal display (LCD) or an electroluminescence (EL) display and various screens such as the display screen shown in FIG. 12 are displayed based on the display signal input from the controller 75. For example, the liquid crystal monitor 87 in FIG. 12 corresponds to the display unit.

The controller 75 is realized by a microprocessor such as a central processing unit (CPU) or a digital signal processor (DSP), a control device such as an application specific integrated circuit (ASIC), and a computing device, and controls collectively the respective units of the liquid ejection system 1. The controller 75 includes a piezoelectric element control unit 751, a pump control unit 756, and a momentum display control unit 757 as a display control unit. Further, the respective units configuring the controller 75 may be configured of hardware such as a dedicated module circuit.

The piezoelectric element control unit 751 includes a rising frequency setting section 752, a voltage magnitude setting section 753, and a repetitive frequency setting section 754. Depending on the dial position of the momentum dial 811 and the dial position of the repetitive frequency dial 813, the rising frequency setting section 752 sets the rising frequency of the drive voltage waveform, the voltage magnitude setting section 753 sets the voltage magnitude of the drive voltage waveform, and the repetitive frequency setting section 754 sets the repetitive frequency of the drive voltage waveform.

The piezoelectric element control unit 751 sets the drive voltage waveform in response to the rising frequency, the voltage magnitude, and the repetitive frequency set by the respective sections 752, 753, and 754 and performs control of applying the drive signal of the set waveform to the piezoelectric element 45. At this time, as a rising shape setting unit, the piezoelectric element control unit 751 changeably sets a shape of a waveform (falling waveform) of a falling portion of the drive voltage waveform in the manner shown in FIG. 10A such that the repetitive frequency becomes a frequency set as the repetitive frequency instructing value by the repetitive frequency setting section 754.

The pump control unit 756 outputs a drive signal to the feeding pump device 20 and drives the feeding pump device 20. The momentum display control unit 757 performs control of displaying a momentum instructing value (that is, a current value of the momentum P) allocated to a dial position of the momentum dial 811 being selected, a repetitive frequency instructing value (that is, a current value of the repetitive frequency) allocated to a dial position of the repetitive frequency dial 813 being selected, and momentum per unit time, which is obtained by multiplying the above values.

The storage unit 77 is realized by various integrated circuit (IC) memories such as read only memory (ROM), flash ROM, or random access memory (RAM), or a recording medium such as a hard disk. In the storage unit 77, a program for causing the liquid ejection system 1 to operate and realizing various functions provided in the liquid ejection system 1, data used during execution of the program, or the like are stored in advance, or the program and the data are temporarily stored for each process.

In addition, in the storage unit 77, a momentum conversion table 771 is stored. The momentum conversion table 771 is a data table in which correspondence relationships among the momentum P, the rising frequency, and the voltage magnitude for each repetitive frequency described above are set with reference to FIG. 11.

FIG. 14 is a diagram showing an example of a data configuration of the momentum conversion table 771. As shown in FIG. 14, the momentum conversion table 771 is a data table in which the dial position (scale) of the repetitive frequency dial 813, the repetitive frequency instructing value allocated to the dial position, the dial position of the momentum dial 811, the momentum instructing value allocated to the dial position, the voltage magnitude, and the rising frequency are associated and a correspondence relationship between the momentum P and the voltage magnitude at a predetermined rising frequency $f\_001$ is set for each repetitive frequency.

With reference to the momentum conversion table 771, the rising frequency setting section 752 fixedly sets the rising frequency to be $f\_001$. The voltage magnitude setting section 753 reads and sets the voltage magnitude corresponding to combination of the respective dial positions of the momentum dial 811 and the repetitive frequency dial 813 being selected, from the momentum conversion table 771, and reads the voltage magnitude corresponding to combination of the dial positions of the respective dials 811 and 813 from the momentum conversion table 771 and the setting is renewed in a case where one of the momentum dial 811 and the repetitive frequency dial 813 is operated.

In addition, the repetitive frequency setting section 754 reads the repetitive frequency instructing value corresponding to the dial position of the repetitive frequency dial 813 being selected from the momentum conversion table 771 and sets the repetitive frequency and reads the repetitive frequency instructing value of the selected dial position from the momentum conversion table 771 and renews the setting of the repetitive frequency in a case where the repetitive frequency dial 813 is operated.

Flow of Process

Figure 15:
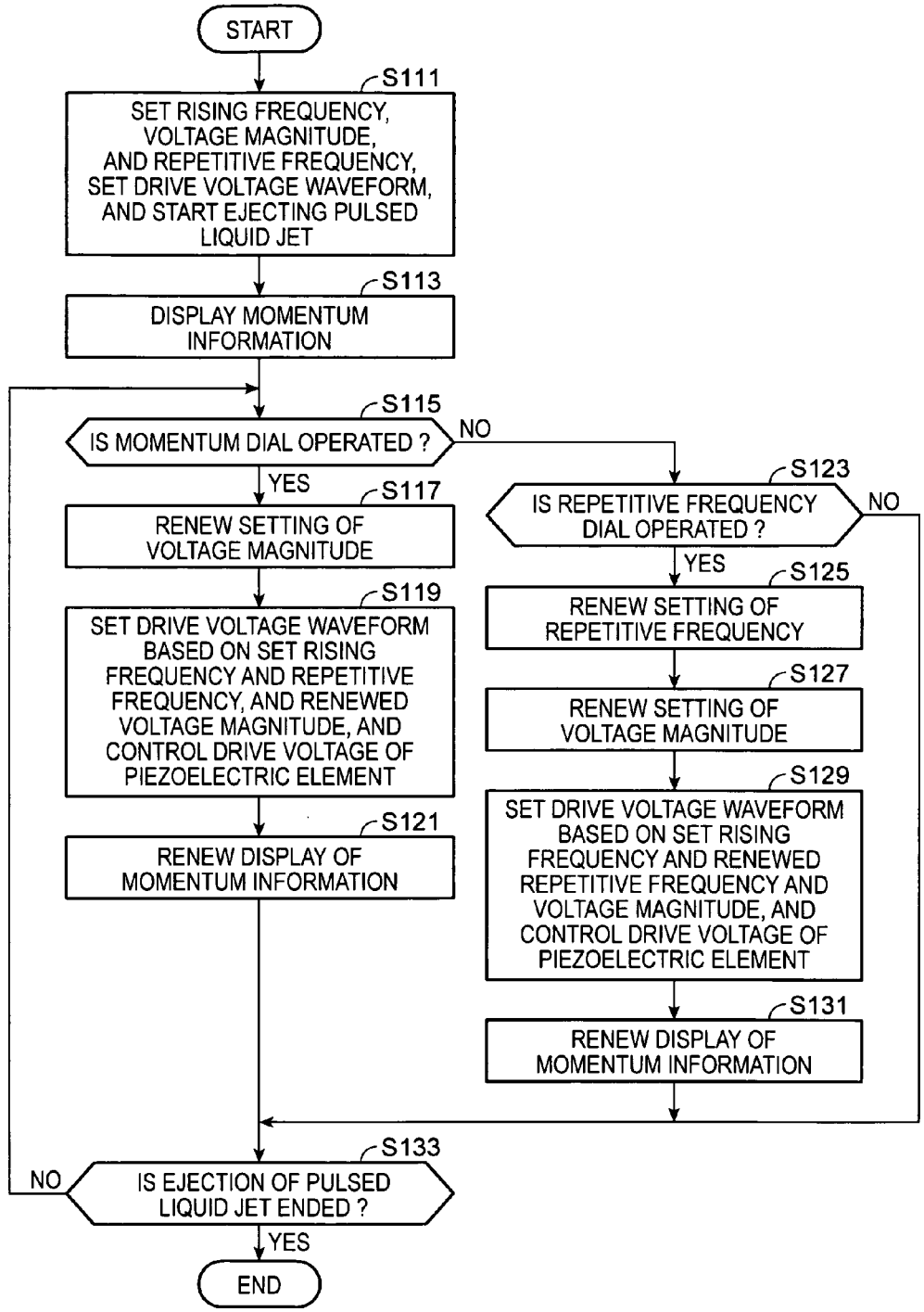
FIG. 15 is a flowchart showing a flow of a process which is performed by a controller during the ejection of a pulsed liquid jet according to Example 1.

FIG. 15 is a flowchart showing a flow of a process which is performed by the controller 75 on the occasion of ejection of a pulsed liquid jet. First, the pump control unit 756 drives the feeding pump device 20, the piezoelectric element control unit 751 drives the piezoelectric element 45, and the ejection of the pulsed liquid jet is started (step S111). At this time, the rising frequency setting section 752 reads and sets the rising frequency set in the momentum conversion table 771, as a fixed value. In addition, the voltage magnitude setting section 753 acquires dial positions of the momentum dial 811 and the repetitive frequency dial 813 being selected and reads and sets the voltage magnitude corresponding to the combination thereof from the momentum conversion table 771. Further, the repetitive frequency setting section 754 reads the repetitive frequency instructing value allocated to the dial position of the repetitive frequency dial 813 being selected from the momentum conversion table 771 and sets the repetitive frequency. Also, the piezoelectric element control unit 751 sets the drive voltage waveform depending on the rising frequency, the voltage magnitude, and the repetitive frequency and applies the drive signal of the set drive voltage waveform to the piezoelectric element 45.

In addition, the momentum display control unit 757 performs control of displaying the momentum information on the display unit 73 (step S113). For example, the momentum display control unit 757 reads the momentum instructing value allocated to the dial position of the momentum dial 811 from the momentum conversion table 771 and the momentum display control unit calculates momentum per unit time, which is a product of the above momentum instructing value and the repetitive frequency instructing value read in step S111. Also, the momentum display control unit 757 performs a display process of the display screen on which the momentum instructing value, the repetitive frequency instructing value, and the momentum per unit time, are displayed as momentum information, on the display unit 73. Further, in terms of the momentum per unit time, a calculation configuration is not limited to a configuration in which calculation is performed in display control of the momentum information and a configuration in which the momentum is set in the momentum conversion table 771 or the like and is read may be employed.

Then, the controller 75 monitors an operation of the momentum dial 811 in step S115 until it is determined that the ejection of the pulsed liquid jet is ended by the operation of the ejection pedal 83 and the ejection button 84 (NO in step S133) and the controller monitors an operation of the repetitive frequency dial 813 in step S123.

Also, in a case where the momentum dial 811 is operated (YES in S115), the voltage magnitude setting section 753 reads the voltage magnitude corresponding to the combination of the selected dial position and the dial position of the repetitive frequency dial 813 being selected from the momentum conversion table 771 and renews the setting of the voltage magnitude (step S117). Then, the piezoelectric element control unit 751 sets the drive voltage waveform depending on the set repetitive frequency, the rising frequency, and the voltage magnitude and applies the drive signal of the set drive voltage waveform to the piezoelectric element 45 (step S119).

In addition, the momentum display control unit 757 reads the momentum instructing value allocated to the selected dial position from the momentum conversion table 771 and performs control of renewal of display on the display unit 73 (step S121).

Meanwhile, in a case where the repetitive frequency dial 813 is operated (YES in step S123), the repetitive frequency setting section 754 reads the repetitive frequency instructing value allocated to the selected dial position from the momentum conversion table 771 and renews the setting of the repetitive frequency (step S125). Subsequently, the voltage magnitude setting section 753 reads the voltage magnitude corresponding to the combination of the selected dial position and the dial position of the momentum dial 811 being selected, from the momentum conversion table 771, and renews the setting of the voltage magnitude (step S127). Then, the piezoelectric element control unit 751 sets the drive voltage waveform depending on the set repetitive frequency, the rising frequency, and the voltage magnitude and applies the drive signal of the set drive voltage waveform to the piezoelectric element 45 (step S129).

In addition, the momentum display control unit 757 reads the repetitive frequency allocated to the selected dial position from the momentum conversion table 771 and performs control of renewal of display on the display unit 73 (step S131).

According to Example 1, a correspondence relationship between the momentum P and the voltage magnitude at the predetermined rising frequency at each repetitive frequency is set in advance. Therefore, it is possible to set the optimal voltage magnitude for achieving the cutting depth and the cutting volume as exact as an operational sense based on the correspondence relationship and to control the drive voltage waveform of the piezoelectric element 45. For example, when the momentum dial 811 moves to a position one scale apart, the momentum P is changed by an amount corresponding to a scale interval. Therefore, it is possible to realize the cutting depth or the cutting volume as intended by a user and as exact as the operational sense and it is possible to improve usability.

In addition, it is possible to increase and decrease the repetitive frequency such that the momentum P becomes the momentum instructing value. Accordingly, when the scale of the momentum dial 811 is not changed and only the scale of the repetitive frequency dial 813 is changed, the cutting depth or the cutting volume is maintained to be constant by the pulsed liquid jet for one pulse, it is possible to adjust the cutting speed as intended to be proportional to the repetitive frequency, and an improvement of the usability is achieved.

Example 2

Figure 16:
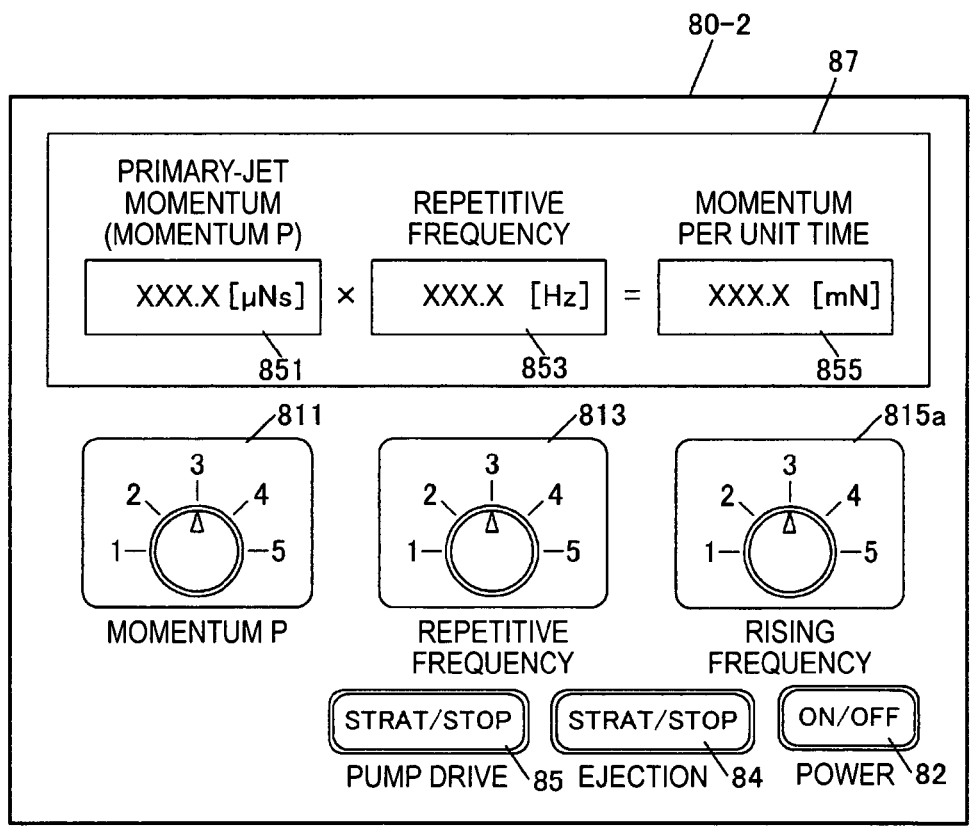
FIG. 16 is a diagram showing an operation panel of a liquid ejection control device according to Example 2.

Next, Example 2 is described. The same signs are assigned to the same components as those in Example 1. FIG. 16 is a diagram showing an operation panel 80-2 provided in a liquid ejection control device 70-2 according to Example 2. As shown in FIG. 16, on the operation panel 80-2, the momentum dial 811, the repetitive frequency dial 813, a rising frequency dial 815a as a third operation unit, the power button 82, the ejection button 84, the pump drive button 85, and the liquid crystal monitor 87 are disposed.

The rising frequency dial 815a is for inputting an instructing value of a rising frequency (rising frequency instructing value) as a third instructing value, and has a configuration in which five-level dial positions, to which, for example, scales of "1" to "5" are assigned, are selectable. Similar to the repetitive frequency dial 813, the rising frequency dial 815a may also have the configuration in which an activate switch is provided. A surgeon increases or decreases the rising frequency in five levels by switching between the dial positions of the rising frequency dial 815a. A rising frequency instructing value is allocated to each position of the dial in advance such that the rising frequency is increased by a constant amount in proportion to a numerical value on a corresponding scale. Further, the number of levels of the dial positions is not limited to five and may be appropriately set. In addition, the number of levels may be different from that of the momentum dial 811 or the repetitive frequency dial 813.

In this manner, in Example 2, three operations performed by a surgeon during surgery are the increase/decrease operation of the momentum P using the momentum dial 811, the increase/decrease operation of the repetitive frequency using the repetitive frequency dial 813, and the increase/decrease operation of the rising frequency using the rising frequency dial 815a, and the correspondence relationship between the momentum P, the rising frequency, and the voltage magnitude for each repetitive frequency is listed in a table. When the momentum P51 shown in FIG. 11 is focused, for example, rising frequencies f61, f62, and the like, having the same frequency interval and voltage magnitudes V61, V62, and the like at intersection points A61, A62, and the like, with each contour line are associated with each other and a data table is made. Also, the rising frequencies f61, f62, and the like, are allocated as the rising frequency instructing values in this order to the respective dial positions 1, 2, and the like of the rising frequency dial 815a.

Figure 17:
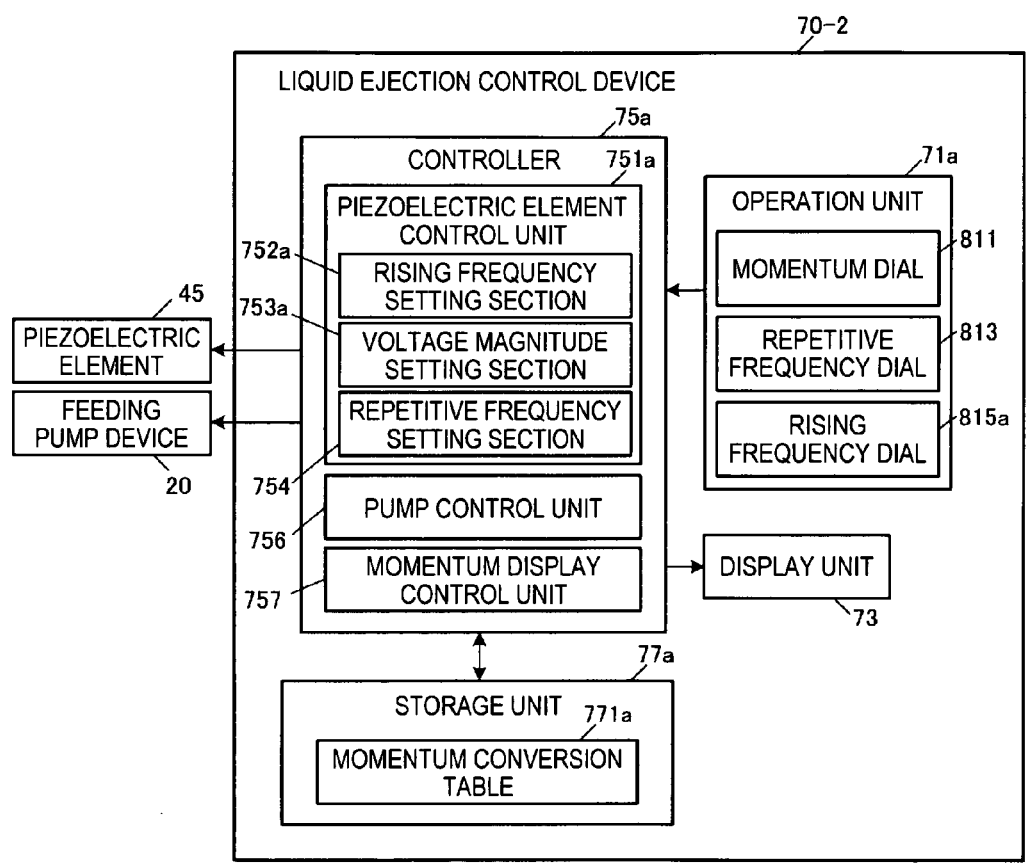
FIG. 17 is a block diagram showing an example of a functional configuration of the liquid ejection control device according to Example 2.

FIG. 17 is a block diagram showing an example of a functional configuration of the liquid ejection control device according to Example 2. As shown in FIG. 17, the liquid ejection control device 70-2 includes an operation unit 71a, the display unit 73, a controller 75a, and a storage unit 77a.

The operation unit 71a includes the momentum dial 811, the repetitive frequency dial 813, and the rising frequency dial 815a.

In addition, the controller 75a includes a piezoelectric element control unit 751a, the pump control unit 756, and the momentum display control unit 757. The piezoelectric element control unit 751a includes a rising frequency setting section 752a, a voltage magnitude setting section 753a, and the repetitive frequency setting section 754.

In the storage unit 77a, a momentum conversion table 771a is stored. FIG. 18 is a diagram showing an example of a data configuration of the momentum conversion table 771a in Example 2. As shown in FIG. 18, the momentum conversion table 771a is a data table in which the dial position (scale) of the repetitive frequency dial 813, the repetitive frequency instructing value allocated to the dial position, the dial position of the momentum dial 811, the momentum instructing value allocated to the dial position, and the dial position of the rising frequency dial 815a, the rising frequency instructing value allocated to the dial position, and the voltage magnitude are associated and a correspondence relationship among the momentum P and the voltage magnitude, and the rising frequency is set for each repetitive frequency.

With reference to the momentum conversion table 771a, the rising frequency setting section 752a reads the rising frequency instructing value corresponding to the dial position of the rising frequency dial 815a being selected, from the momentum conversion table 771a and sets the rising frequency, and the repetitive frequency setting section reads the rising frequency instructing value of the selected dial position from the momentum conversion table 771a and renews the setting of the rising frequency in a case where the rising frequency dial 815a is operated. The voltage magnitude setting section 753a reads and sets the voltage magnitude corresponding to combination of the respective dial positions of the momentum dial 811, the repetitive frequency dial 813, and the rising frequency dial 815a, being selected from the momentum conversion table 771a, and reads the voltage magnitude corresponding to combination of the dial positions of the respective dials 811,813, and 815a from the momentum conversion table 771a and the setting is renewed in a case where one of the momentum dial 811, the repetitive frequency dial 813, and the rising frequency dial 815a is operated.

Flow of Process

Figure 19:
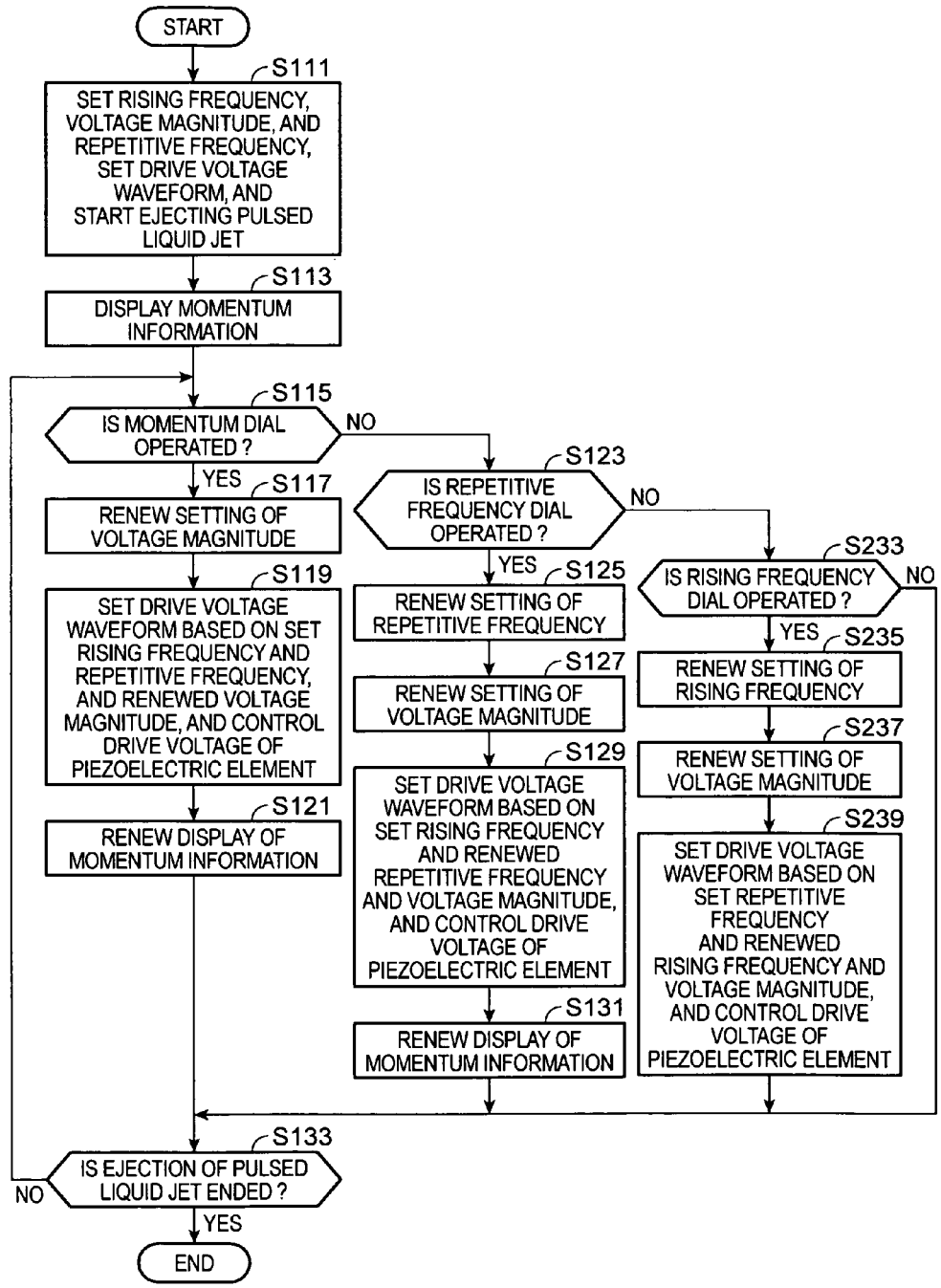
FIG. 19 is a flowchart showing a flow of a process which is performed by a controller on the occasion of ejection of a pulsed liquid jet according to Example 2.

FIG. 19 is a flowchart showing a process which is performed by the controller 75a on the occasion of ejection of a pulsed liquid jet. Further the same signs are assigned to the same processes as those in FIG. 15.

In Example 2, in step S111, the rising frequency setting section 752a reads the rising frequency instructing value allocated to the dial position of the rising frequency dial 815a being selected from the momentum conversion table 771a and sets the rising frequency.

In addition, in step S233, the operation of the rising frequency dial 815a is monitored. Also, in a case where the rising frequency dial 815a is operated (YES in step S233), the rising frequency setting section 752a reads the rising frequency instructing value allocated to the selected dial position from the momentum conversion table 771a and renews the setting of the rising frequency (step S235). Subsequently, the voltage magnitude setting section 753a reads the voltage magnitude corresponding to the combination of the selected dial position and the respective dial positions of the momentum dial 811 and the rising frequency dial 815a being selected from the momentum conversion table 771a and renews the setting of the voltage magnitude (step S237). Then, the piezoelectric element control unit 751a sets the drive voltage waveform depending on the set repetitive frequency, the rising frequency, and the voltage magnitude and applies the drive signal of the set drive voltage waveform to the piezoelectric element 45 (step S239).

According to Example 2, a correspondence relationship between the momentum P, the rising frequency, and the voltage magnitude is set for each repetitive frequency in advance and it is possible to control the drive voltage waveform of the piezoelectric element 45 such that the momentum P becomes the momentum instructing value even when the rising frequency is increased or decreased.

Further, in the embodiment described above, the case where the momentum P is increased or decreased in a stepwise manner through an operation of the momentum dial 811, the case where the repetitive frequency is increased or decreased in a stepwise manner through an operation of the repetitive frequency dial 813, and the case where the rising frequency is increased or decreased in a stepwise manner through an operation of the rising frequency dial 815a, are described. In comparison, the respective dials 811, 813, 815a may have a configuration in which the momentum instructing value, the repetitive frequency instructing value, or the rising frequency instructing value can be steplessly adjusted even at a position (intermediate position) between the dials to which scales are assigned.

As a specific process, for example, when the momentum dial 811 is focused and a dial position between the scales is selected, with reference to the momentum conversion table 771 (FIG. 14) or the momentum conversion table 771a (FIG. 18), the momentum instructing value associated with the dial position of the scales before and after the selected momentum P and the voltage magnitudes corresponding to these momentum instructing values are read. Also, linear interpolation is performed using the respective read voltage magnitudes and a voltage magnitude corresponding to the momentum P between currently selected dial positions is specified.

In order to achieve higher accuracy, the voltage magnitudes corresponding to the dial positions (momentum instructing values) of not only the scales before and after, but also scales before and after one scale further of the selected momentum P may be read. Also, polynomial interpolation may be performed using the respective read voltage magnitudes and a voltage magnitude corresponding to the momentum P between the currently selected dial positions may be specified.

In addition, even in a case where the position (intermediate position) between the dial positions of the repetitive frequency dial 813 or the rising frequency dial 815a is selected, it is possible to specify a voltage magnitude by performing the same interpolation.

In addition, in the embodiment described above, as described with reference to FIG. 10A, in order to increase and decrease the repetitive frequency, the rising shape is changeably set. In comparison, the entire drive voltage waveform is simply widened or contracted in the time axis direction, and thereby the repetitive frequency may be increased and decreased. In this case, a simulation, which is performed when the momentum conversion tables 771 and 771a are made, is performed while the repetitive frequency is changed in the manner described above.

In addition, in the embodiment described above, the rising frequency is illustrated as a rising index value. In comparison, instead of the repetitive frequency, the rising time Tpr may be used.

In addition, the momentum dial 811, the repetitive frequency dial 813, and the rising frequency dial 815a are not limited to a case of being realized by a dial switch and, for example, the dials may be realized by a lever switch, a button switch, or the like. In addition, the dials may be realized by a key switch through software, or the like, with the display unit 73 as a touch panel. In this case, a user operates the touch panel which is the display unit 73 and inputs the momentum instructing value, the repetitive frequency instructing value, and the rising frequency instructing value.

In addition, in the embodiment described above, the piezoelectric element control units 751 and 751a are described to set the drive voltage waveform depending on the set rising frequency, the voltage magnitude, and the repetitive frequency (for example, step S111, S119, or the like in FIG. 15). In comparison, for each one of the possible combinations of the rising frequency, the voltage magnitude, and the repetitive frequency, the drive voltage waveform for one cycle may be generated in advance and may be stored as waveform data associated with the corresponding combination, in the storage units 77 and 77a. Also, the waveform data corresponding to the combination of the set rising frequency, the voltage magnitude, and the repetitive frequency may be read and a drive signal depending on the read waveform data may be applied to the piezoelectric element 45.

In addition, in the embodiment described above, a configuration, in which the pulsed liquid jet having the momentum in the range from 2 [nNs] to 2 [mNs] or the kinetic energy in the range from 2 [nJ] to 200 [mJ] is ejected, is disclosed and more preferably, a configuration, in which the pulsed liquid jet having the momentum in the range from 20 [nNs] to 200 [μNs] or the kinetic energy in the range from 40 [nJ] to 10 [mJ] is ejected, may be employed. In this manner, it is possible to appropriately cut a living tissue or a gel material.

What is claimed is:

1. A liquid ejection control device in which a predetermined drive voltage waveform is applied to a piezoelectric element to control the ejection of a pulsed liquid jet of liquid having a pulsed shape from a liquid ejection device that uses the piezoelectric element, the liquid ejection control device comprising:
   a first operation unit for inputting a first instructing value related to momentum of the pulsed liquid jet;
   a second operation unit for inputting a second instructing value related to a number of times an ejection of the pulsed liquid is performed per unit time; and
   a voltage magnitude setting section that sets voltage magnitude of the drive voltage waveform such that the momentum becomes the first instructing value, based on an index value related to rising of the drive voltage waveform and the second instructing value.

2. The liquid ejection control device according to claim 1, further comprising:
   a third operation unit for inputting a third instructing value related to the index value.

3. A liquid ejection system comprising:
   the liquid ejection control device according to claim 2;
   a liquid ejection device; and
   a feeding pump device.

4. The liquid ejection control device according to claim 1, further comprising:
   a falling shape setting section that changeably sets a falling shape of the drive voltage waveform depending on the second instructing value.

5. A liquid ejection system comprising:
   the liquid ejection control device according to claim 4;
   a liquid ejection device; and
   a feeding pump device.

6. The liquid ejection control device according to claim 1, further comprising:
   a display control unit that performs control of display of at least one of the first instructing value and the second instructing value.

7. A liquid ejection system comprising:
   the liquid ejection control device according to claim 6;
   a liquid ejection device; and
   a feeding pump device.

8. The liquid ejection control device according to claim 1, wherein the liquid ejection device is controlled such that the pulsed liquid jet has momentum in a range from 2 [nNs (nanonewton seconds)] to 2 [mNs (millinewton seconds)] or kinetic energy in a range from 2 [nJ (nanojules)] to 200 [(mJ (millijules)].

9. A liquid ejection system comprising:
   the liquid ejection control device according to claim 8;
   a liquid ejection device; and
   a feeding pump device.

10. The liquid ejection control device according to claim 1, wherein the liquid ejection device is controlled to cut a living tissue using the pulsed liquid jet.

11. A liquid ejection system comprising:
    the liquid ejection control device according to claim 10;
    a liquid ejection device; and
    a feeding pump device.

12. A liquid ejection system comprising:
    the liquid ejection control device according to claim 1;
    a liquid ejection device; and
    a feeding pump device.

13. A control method in which a predetermined drive voltage waveform is applied to a piezoelectric element to control the ejection of a pulsed liquid jet of liquid having a pulsed shape from a liquid ejection device that uses the piezoelectric element, the control method comprising:
    inputting a first instructing value related to momentum of the pulsed liquid jet;
    inputting a second instructing value related to the number of times an ejection of the pulsed liquid is performed per unit time; and
    setting voltage magnitude of the drive voltage waveform such that the momentum becomes the first instructing value, based on an index value related to rising of the drive voltage waveform and the second instructing value.

* * * * *